(12) United States Patent
Murphy et al.

(10) Patent No.: US 10,065,985 B2
(45) Date of Patent: Sep. 4, 2018

(54) METHOD FOR FULLY AUTOMATED SYNTHESIS OF 16β-$^{18}$F-FLUORO-5α-DIHYDROTESTOSTERONE ($^{18}$F-FDHT)

(71) Applicant: THE REGENTS OF THE UNIVERSITY OF CALIFORNIA, Oakland, CA (US)

(72) Inventors: Jennifer Marie Murphy, Los Angeles, CA (US); Mark Saul Lazari, Norwalk, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/545,924

(22) PCT Filed: Feb. 3, 2016

(86) PCT No.: PCT/US2016/016450
§ 371 (c)(1),
(2) Date: Jul. 24, 2017

(87) PCT Pub. No.: WO2016/126875
PCT Pub. Date: Aug. 11, 2016

(65) Prior Publication Data
US 2018/0016296 A1    Jan. 18, 2018

Related U.S. Application Data

(60) Provisional application No. 62/111,559, filed on Feb. 3, 2015.

(51) Int. Cl.
*C07J 75/00* (2006.01)
*B01J 19/00* (2006.01)
*C07J 31/00* (2006.01)
*C07J 21/00* (2006.01)
*C07J 1/00* (2006.01)

(52) U.S. Cl.
CPC ........... *C07J 31/006* (2013.01); *B01J 19/004* (2013.01); *B01J 19/0093* (2013.01); *C07J 1/0022* (2013.01); *C07J 21/006* (2013.01); *B01J 2219/00813* (2013.01); *B01J 2219/00889* (2013.01); *C07J 75/00* (2013.01)

(58) Field of Classification Search
None
See application file for complete search history.

(56) References Cited

FOREIGN PATENT DOCUMENTS

WO    2011/073286 A1    6/2011
WO    2014/160799 A1    10/2014

OTHER PUBLICATIONS

Beattie, Bradley J., Pharmacokinetic Assessment of the Uptake of 16B-18F-Fluoro-5a-Dihydrotestoterone (FDHT) in Prostate Tumors as Measured by PET, Journal of Nuclear Medicine, published on Jan. 15, 2010 as doi:10.2967/numed.109.066159, Pharmacokinetic Assessment of 18F-FDHT; pp. 183-192.

Guillouet, Stephane et al., Fully Automated Radiosynthesis of 2-[18F]Fludarabine for PET Imaging of Low-Grade Lymphoma, Mol Imaging Biol (2014) 16:28-35.

Haslop, Anna et al., Fully automated radiosynthesis of [1-(2-[18F]fluoroethyl),1H[1,2,3]triazole 4-ethylene] triphenylphosphonium bromide as a potential positron emission tomography tracer for imaging apoptosis, J. Label Compd. Radiopharm 2013, 56, 313-316.

Lazari, Mark et al., ELIXYS—a fully automated, three-reactor high-pressure radiosynthesizer for development and routine production of diverse PET tracers, EJNMMI Research 2013, 3:52, http://www.ejnmmires.com/content/3/1/52.

Lazari, Mark et al., Fully-automated synthesis of 16B-18F-fluoro-5a-dihydrotestosterone (FDHT) on the ELIXYS radiosynthesizer, Applied Radiation and Isotopes 103 (2015) 9-14.

Lazari, Mark et al., Fully Automated Production of Diverse 18F-Labeled PET Tracers on the ELIXYS Multireactor Radiosynthesizer Without Hardware Modification, J Nucl Med Technol 2014; 42:203-210.

LARSON, Steven M. et al., Tumor Localization of 16B-18F-Fluoro-5a-Dihydrotestosterone Versus 18F-FDG in Patients with Progressive, Metastic Prostate Cancer, J Nucl Med. 2004; 45:366-373.

Liu, Aijun et al., Fluorine-18-Labeled Androgens: Radiochemical Synthesis and Tissue Distribution Studies on Six Fluorine-Substituted Androgens, Potential Imaging Agents for Prostatic Cancer, J Nucl Med. 1992; 33:724-734.

Mori, Tetsuya et al., Automated synthesis of 16B-[18F]fluoro-5a-dihyrotestosterone using a plastic cassette-type FDG synthesizer, J Nucl Med, May 2010, vol. 51, No. Supplement 2, Abstract 1525.

Nickels, M.L. et al., Preclinical Evaluation of 7-Chloro-N,N,5-trimethyl-4-oxo-3(6-[F]fluoropyridin-2-yl)-3,5-dihydro-4H-pyridazino[4,5-b]indole-1-acetamide: A Novel Pyridazinoindole Ligand for PET Imaging of TSPO in Cancer, Wold Molecular Imaging Congress, 2014, Abstract LBA 12.

Zhou, Dong et al., Optimization of the preparation of fluorine-18-labeled steroid receptor ligands 16alpha-[18F]fluoroestradiol (FES), [18F]fluoro furanyl norprogesterone (FFNP), and 16beta-[18F]fluoro-5alpha-dihydrotestosterone (FDHT) as radiopharmaceuticals, J. Label Compd. Radiopharm 2014, 57, 371-377.

(Continued)

*Primary Examiner* — Samantha L Shterengarts
(74) *Attorney, Agent, or Firm* — Vista IP Law Group LLP

(57) ABSTRACT

The automated synthesis of clinically relevant amounts of 16β-$^{18}$F-fluoro-5α-dihydrotestosterone ($^{18}$F-FDHT) using a commercially available radiosynthesizer. Synthesis was performed in 90 minutes with a decay-corrected radiochemical yield of 29±5%. The specific activity was 4.6 Ci/μmol (170 GBq/μmol) at end of formulation with a starting activity of 1.0 Ci (37 GBq). The formulated $^{18}$F-FDHT yielded sufficient activity for multiple patient doses and passed all quality control tests required for routine clinical use.

14 Claims, 12 Drawing Sheets

(56) References Cited

OTHER PUBLICATIONS

PCT International Search Report for PCT/US2016/016450, Applicant: The Regents of the University of California, Form PCT/ISA/210 and 220, dated May 13, 2016 (6pages).
PCT Written Opinion of the International Search Authority for PCT/US2016/016450, Applicant: The Regents of the University of California, Form PCT/ISA/237, dated May 13, 2016 (5pages).
PCT International Preliminary Report on Patentability (Chapter I of the Patent Cooperation Treaty) for PCT/US2016/016450, Applicant: The Regents of the University of California, Form PCT/IB/326 and 373, dated Aug. 17, 2017 (7pages).

REACT
POSITION #2

ADDITION

TRANSFER

ADDITION

METHOD FOR FULLY AUTOMATED SYNTHESIS OF 16β-$^{18}$F-FLUORO-5α-DIHYDROTESTOSTERONE ($^{18}$F-FDHT)

RELATED APPLICATION

This Application is a U.S. National Stage filing under 35 U.S.C. § 371 of International Application No. PCT/US2016/016450, filed Feb. 3, 2016, which claims priority to U.S. Provisional Patent Application No. 62/111,559 filed on Feb. 3, 2015, which are hereby incorporated by reference. Priority is claimed pursuant to 35 U.S.C. §§ 119, 371 and any other applicable statute.

TECHNICAL FIELD

The technical field generally relates to automated methods for manufacturing positron emission tomography (PET) probes and in particular automated methods for manufacturing 16β-$^{18}$F-fluoro-5α-dihydrotestosterone ($^{18}$F-FDHT).

BACKGROUND

Prostate cancer has become and remains the second leading cause of cancer-related death in American men. Effective management of prostate cancer requires early detection and the availability of accurate diagnostic modalities for predicting and monitoring the disease. Increased androgen receptor (AR) expression in primary tumors of prostate cancer is a strong indicator of the disease; however, due to heterogeneity of the tumors, biopsy samples alone may not be sufficient for disease detection. Molecular imaging agents that can noninvasively provide prognostic information for distinguishing AR-positive tumors are critically important for the treatment of prostate cancer. Over the years, a number of fluorinated androgen derivatives have been synthesized and evaluated for AR binding and tissue distribution in vivo using positron emission tomography (PET). Several promising candidates have been successfully labeled with the positron emitting radionuclide fluorine-18 in efforts to develop PET tracers for tumor localization in patients with metastatic prostate cancer. For example, 16β-$^{18}$F-fluoro-5α-dihydrotestosterone ($^{18}$F-FDHT), a fluorinated analog of the native AR-binding ligand dihydrotestosterone, has been studied in both rat and primate models and has proven to be one of the most effective in vivo AR-binding radiotracers studied to date.

Significant interest in evaluating and monitoring AR expression in prostate cancer patients has led to multiple clinical studies using $^{18}$F-FDHT. The overall goal of these studies was to assess the potential of $^{18}$F-FDHT as a diagnostic tool for imaging AR expression in prostate cancer patients. In these studies, $^{18}$F-FDHT was found to bind AR in both primary tumor and metastatic sites suggesting its crucial role in prostate cancer imaging. Clinical efficacy proved promising, even when compared to $^{18}$F-FDG in patients with castrate-resistant prostate cancer. More recently, a study by Beattie et al. evaluated the pharmacokinetic properties of $^{18}$F-FDHT and found that uptake of the tracer in prostate tumors correlated reasonably well with AR expression in metastatic prostate cancer. Beattie et al., Pharmacokinetic Assessment of the Uptake of 16β-18F-Fluoro-5α-Dihydrotestosterone (FDHT) in Prostate Tumors as Measured by PET. J. Nucl. Med. 51, 183-192 (2010). As more clinical studies are conducted, the potential of $^{18}$F-FDHT to elucidate the role of AR expression in metastatic prostate cancer becomes clearer and may lead to improved therapeutic approaches and clinical management of the disease.

The manual synthesis of $^{18}$F-FDHT was reported by Liu et al. (1992b) via the precursor (precursor 1) 16α-[[(trifluoromethyl)sulfonyl]oxy]-3,3-(ethylenedioxy)androstan-17-one (as illustrated in FIG. 1). Nucleophilic displacement of the triflate of precursor 1 with nBu$_4$N$^{18}$F gave the fluorinated intermediate 2, which underwent subsequent reduction via lithium aluminum hydride (LiAlH$_4$) to afford the α-hydroxyl intermediate 3. Acid-catalyzed deprotection of the ketal yielded the desired compound, $^{18}$F-FDHT, in three total steps. The total synthesis time for the manual process, including high-performance liquid chromatography (HPLC) purification, was 90 min. The reported decay-corrected radiochemical yield (RCY) was 31%-48%, and the specific activity was 1.2 Ci/μmol (43 GBq/μmol).

The demand for $^{18}$F-FDHT is expected to increase as the clinical potential of this PET tracer to predict AR expression levels in prostate cancer patients is being recognized. Currently, the clinical production of $^{18}$F-FDHT is generally performed manually by trained radiochemists; as such, its widespread use is limited to a few sites. Due to the highly reactive nature of LiAlH$_4$ the highly exothermic reduction step in the manual synthesis process is performed at −78° C. to tame the reactivity of the reducing reagent and also to minimize the formation of unwanted side products. Automation of this synthesis would enable many more facilities currently equipped for PET synthesis to routinely obtain $^{18}$F-FDHT without the need for specialized personnel. Automated radiosynthesizers, however, do not include the ability to perform reduction reactions at such low temperatures.

SUMMARY

In one embodiment, a method for the automated synthesis of 16β-$^{18}$F-fluoro-5α-dihydrotestosterone ($^{18}$F-FDHT) includes loading a plurality of reagents in an automated radiosynthesizer. The automated radiosynthesizer may include a cartridge-based radiosynthesizer that uses various cartridges in combination with moveable reactor vessels to perform various unit operations of the synthesis protocol. The automated radiosynthesizer includes a programmable control system that interfaces with various hardware components of the radiosynthesizer. For example, a computing device (e.g., client device) can be used to interface and program the radiosynthesizer to perform a predetermined set of unit operations on reagents that contained in the automated radiosynthesizer that collectively together define the radiosynthesis process.

The ELIXYS radiosynthesizer (SOFIE BIOSCIENCES, Culver City, Calif.) is an automated radiochemical synthesizer that can be used for the automated synthesis of 16β-$^{18}$F-fluoro-5α-dihydrotestosterone ($^{18}$F-FDHT). The ELIXYS platform allows one to build syntheses from scratch. The platform uses a three-reactor radiosynthesizer that can be used to perform single and multi-pot synthesis reactions. Fully sealed reactions (between reactor vessels and cartridges) can be performed at high temperatures (up to 200° C.) and pressures (>150 psi) using a moveable reactor system that interfaces with one or more cartridges that provide a housing for all wetted paths and also provides a location to hold reagents that stay sealed and safe from moisture and air until just before addition. The ELIXYS radiosynthesizer also utilizes an intuitive, drag-and-drop user interface as part of the control software such that unit operations may be constructed in sequence to perform the desired syntheses. As described herein, the radiosynthesis method leverages the flexible nature of the ELIXYS radiosynthesizer to fully automate the synthesis of $^{18}$F-FDHT without the need for substantial modification of the conventional synthesis methodology. The method may utilize two cartridges and two reactors in one embodiment, however, in other embodiments, only a single cartridge and a single reactor may be employed.

This method described herein is a fully automated process in which $^{18}$F-FDHT is synthesized on an ELIXYS automated synthesizer, without any intervention or manipulation by the ELIXYS operator. While the protocol described herein has been described in the context of the ELIXYS proprietary automated synthesizer, the protocol could also be implemented on additional commercial radiosynthesizers besides ELIXYS. An advantage of the invention is that it provides better reproducibility in synthesizing $^{18}$F-FDHT. The protocol also lowers the radiation exposure for the operator because no intervention is required or manipulation by the operator. The method enables translation to multiple PET research sites that have an ELIXYS automated synthesizer, enabling clinical trials and other clinical or research use. In addition, production does not require a specifically trained radiochemist.

In one embodiment, $^{18}$F-fluoride is introduced into a reaction container (e.g., vial) that is contained in the automated radiosynthesizer, in the form of tetra-n-butylammonium fluoride (nBu$_4$N$^{18}$F), and the solution is evaporated (e.g., by contacting the vial with an interface surface of a cartridge located above the vial). Acetonitrile is added into the reaction container (via a cartridge) and the contents thereof are again evaporated. The reaction container is then cooled and a precursor solution comprising 16α-[[(trifluoromethyl)sulfonyl]oxy]-3,3-(ethylenedioxy)androstan-17-one (precursor 1) is added. The precursor solution is heated within the reaction container to elevated temperature under stirring conditions. The reaction container is cooled to approximately room temperature and a solution of LiAlH$_4$ is added slowly followed by stirring. Acetone-THF solution is slowly added into the reaction container followed by stirring. HCl solution is added into the reaction container and the reaction container is heated to elevated temperature under stirring conditions. The reaction container is cooled and the contents are transferred through an HLB cartridge so as to trap product therein. The reaction container and the HLB cartridge are rinsed with water. The HLB cartridge is dried under an inert gas. DCM is passed into the HLB cartridge so as to elute $^{18}$F-FDHT from the HLB cartridge. The $^{18}$F-FDHT can then be purified using HPLC and reformulated in ethanol and sterile saline.

In one embodiment, a method for the automated synthesis of 16β-$^{18}$F-fluoro-5α-dihydrotestosterone ($^{18}$F-FDHT) includes loading a plurality of reagents in an automated radiosynthesizer, the automated radiosynthesizer comprising a cassette and a reactor disposed beneath the cassette, wherein at least some of the reagents are stored on the cassette. A synthesis program is executed on the automated radiosynthesizer, the synthesis program including instructions for: eluting $^{18}$F-fluoride into a reactor vial contained in the reactor via the cassette; adding acetonitrile reagent via the cassette into the reactor vial and evaporating the contents thereof with the reactor; cooling the reactor vial and adding a precursor solution comprising 16α-[[(trifluoromethyl)sulfonyl]oxy]-3,3-(ethylenedioxy)androstan-17-one via the cassette; reacting the precursor solution within the reactor vial at elevated temperature under stirring conditions; cooling the reactor vial to approximately room temperature and adding a solution of LiAlH$_4$ via the cassette followed by stirring; adding acetone-THF solution into the reactor vial via the cassette followed by stirring; adding HCl solution into the reactor vial via the cassette and reacting the same at elevated temperature under stirring conditions; cooling the reactor vial and transferring the contents through a hydrophilic-lipophilic balanced (HLB) cartridge so as to trap product therein; rinsing the reaction container and the HLB cartridge with water; drying the HLB cartridge under an inert gas; and passing dichloromethane (DCM) reagent into the HLB cartridge so as to elute $^{18}$F-FDHT from the HLB cartridge.

In another embodiment, a method for the automated synthesis of 16β-$^{18}$F-fluoro-5α-dihydrotestosterone ($^{18}$F-FDHT) includes loading a plurality of reagents in an automated radiosynthesizer, the radiosynthesizer comprising a first reactor, a second reactor, a first cassette disposed above the first reactor, and a second cassette disposed above the second reactor, wherein each of the first and second cassettes define fluid passageways for reagents and reaction products and provide respective contact surfaces for vials respectively contained in the first and second reactors. A synthesis program is executed on the automated radiosynthesizer, the synthesis program including instructions for: eluting $^{18}$F-fluoride into the vial of the first reactor through the first cassette; adding acetonitrile into the vial of the first reactor through the first cassette; contacting the vial of the first reactor against the first cassette and evaporating the contents; cooling the vial of the first reactor and adding a precursor solution comprising 16α-[[(trifluoromethyl)sulfonyl]oxy]-3,3-(ethylenedioxy)androstan-17-one through the first cassette; heating the precursor solution within the vial of the first reactor at elevated temperature under stirring conditions; cooling the vial of the first reactor to approximately room temperature and adding a solution of LiAlH$_4$ via the first cassette followed by stirring; adding acetone-THF solution via the first cassette into the vial of the first reactor followed by stirring; adding HCl solution via the first cassette and heating to elevated temperature under stirring conditions; cooling the vial of the first reactor and transferring the contents through a hydrophilic-lipophilic balanced (HLB) cartridge coupled to the first cassette so as to trap product therein and transferring waste $^{18}$F-fluoride to a waste vial coupled to the first cassette; rinsing the vial of the first reactor and the HLB cartridge with water via the first cassette; drying the HLB cartridge under an inert gas; passing dichloromethane (DCM) through the first cassette and into the HLB cartridge so as to elute $^{18}$F-FDHT from the HLB cartridge and transferring the same to the vial of the second reactor via the second cassette; and transferring the contents of the vial of the second reactor via the second cassette into an HPLC loop associated with the automated radiosynthesizer to purify the $^{18}$F-FDHT. Optionally, one or more downstream desiccant cartridges may be used in one or more embodiments described herein depending on the HPLC loop used.

DETAILED DESCRIPTION OF THE ILLUSTRATED EMBODIMENTS

Radiosynthesizer

Figure 1:
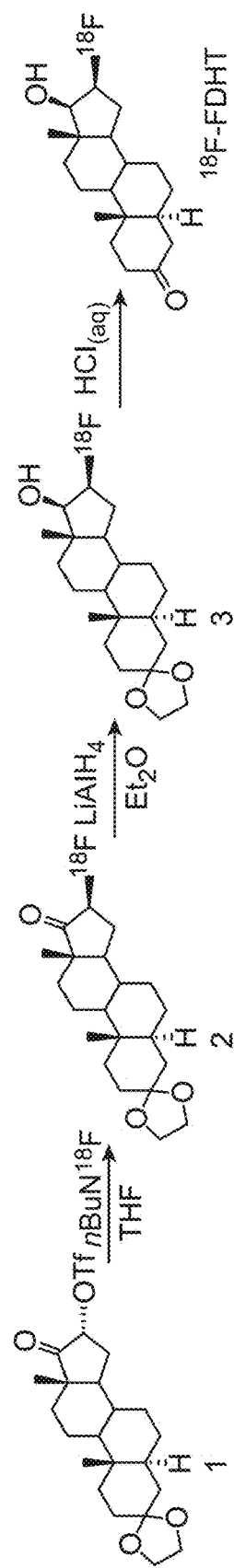
FIG. 1 illustrates a three step process used to synthesize $^{18}$F-FDHT using the automated radiosynthesizer.
Figure 2:
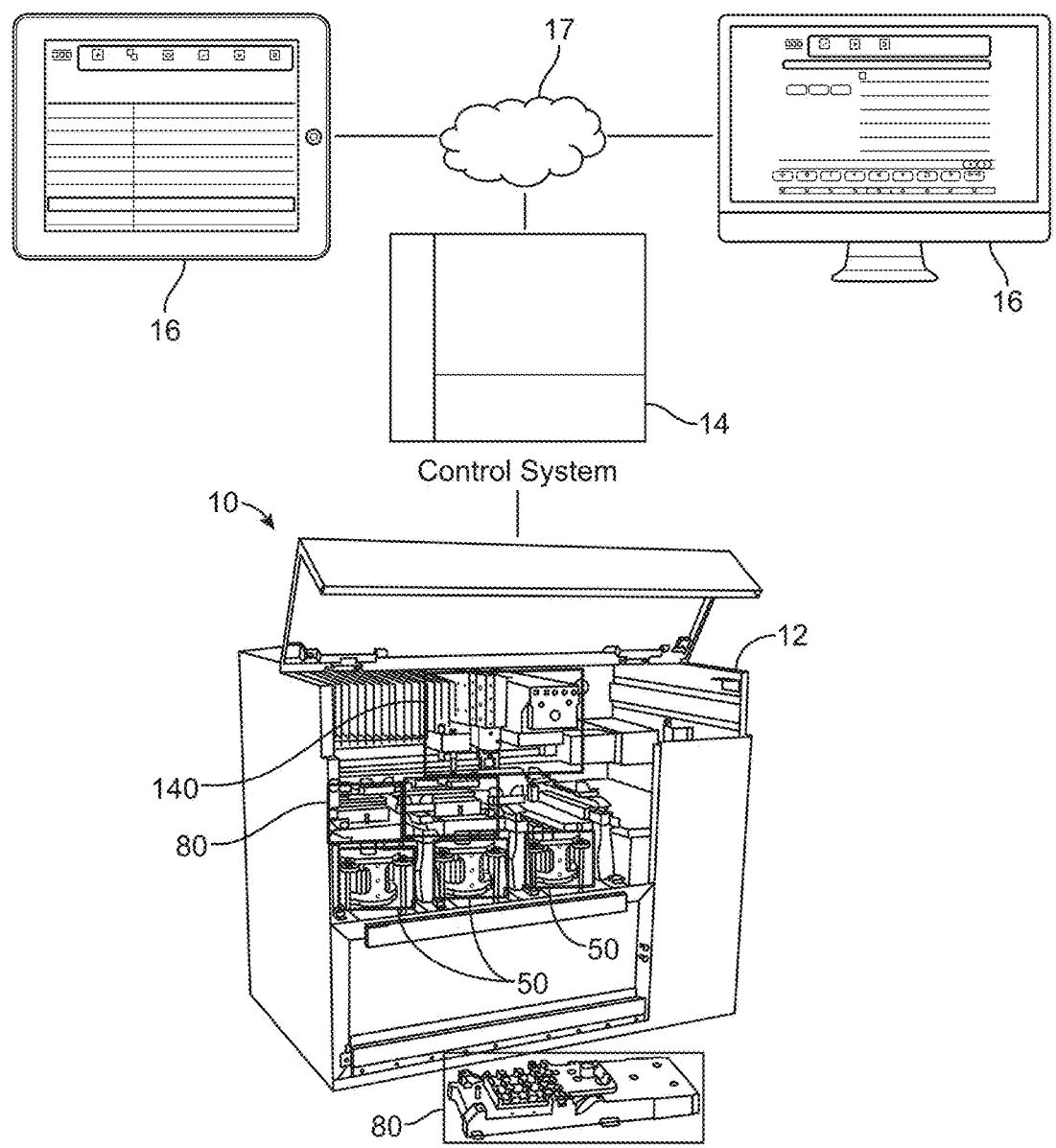
FIG. 2 illustrates an automated radiosynthesizer according to one embodiment.

FIG. 2 illustrates an automated radiosynthesizer 10 according to one embodiment that was used to synthesize $^{18}$F-FDHT. The illustrated automated radiosynthesizer 10 is an ELIXYS automated radiosynthesizer (Sofie Biosciences, Inc.; Culver City, Calif., USA). The automated radiosynthesizer 10 includes a synthesizer 12 where the chemical operations take place to generate a desired radiochemical product such as PET tracer (i.e., $^{18}$F-FDHT). The synthesizer 12 is controlled by control system 14 that interfaces with the synthesizer 12. The control system 14 is used to drive the various hardware components of the synthesizer 12 as described in more detail below. In one aspect of the invention, various client devices 16 (e.g., computing devices) can interface with the control system 14 to operate the automated radiosynthesizer 10. For example, the client devices 16 can be used to create or edit various synthesis programs to produce a desired radiochemical product. The client devices 16 may also be used to observe a radiosynthesis run that is currently in progress. Observation may include data as well as images of the operations taking place in the synthesizer 12 using a camera or the like. The client devices 16 may include a computer such as a laptop or desktop computer or client devices may include mobile devices such as tablets (e.g., Apple iPad, iPhone, and the like), Smartphones (e.g., phones running Google's Android software) and the like. The client devices 16 can interface with the control system 14 using either a dedicated application running on the client device 16 or by using a web browser application. The software that is used as part of the client device 16 may run on a number of different operating systems. Client devices 16 interface with the control system 14 over a network 17 such as a LAN, WAN, or the like. Connections may be wired or wireless.

As explained herein, the client device 16 can be used to create or edit various synthesis programs to produce the desired radiochemical product. Prior radiochemistry systems are typically programmed at the level of individual valves and other components, requiring a detailed understanding of the underlying system hardware. Such an approach necessitates a significant learning curve to become familiar with the particular system details and the programming language/interface such that creation and optimization of a desired synthesis can be accomplished. The software used with the client device 16 uses a different paradigm that strives to eliminate these unnecessary complexities and instead allows the end user to describe the synthesis in terms that make intuitive sense to a chemist or radiochemist that may have no prior experience with automated systems.

A new synthesis protocol is created in two stages: (1) the reagents that will be used in the synthesis are described, and (2) the program is built by stringing together an ordered sequence of unit operations. The user can switch back and forth between these stages with the caveat that the unit operations cannot be fully configured until the relevant reagents have been defined. Rather than creating all new synthesis programs from scratch, it is also possible to copy an existing synthesis protocol and use that as the starting point. Unit operations refer to those fundamental or building block operations or steps that are employed the radiochemical synthesis process. Examples of unit operations include: INITIALIZE (initializes synthesizer for start of run); ADD (for adding a reagent to a reaction vessel); EVAPORATE (for evaporating the contents of a reaction vessel); TRANSFER (for transferring the contents of one reactor to a next reactor); REACT (seals the reactor vessel to the underside of a disposable cassette and heats); PROMPT (pauses sequence run and prompts the user); INSTALL (moves a reactor to the install position for reaction vessel removal and/or installation and prompts the user); TRAP F18 (traps $^{18}$F-Fluoride on a quaternary methylammonium (QMA) cartridge); ELUTE F18 (uses a reagent to elute $^{18}$F-Fluoride off a QMA cartridge); MIX (mixes the contents of a reactor by stirring); EXTERNAL ADD (allows the user to externally add a reagent via tubing); TRANSFER TO HPLC (transfers the contents of the reactor to the HPLC injection loop); MEASURE RADIATION (measures the radiation levels observed in the reactor).

Figure 3:
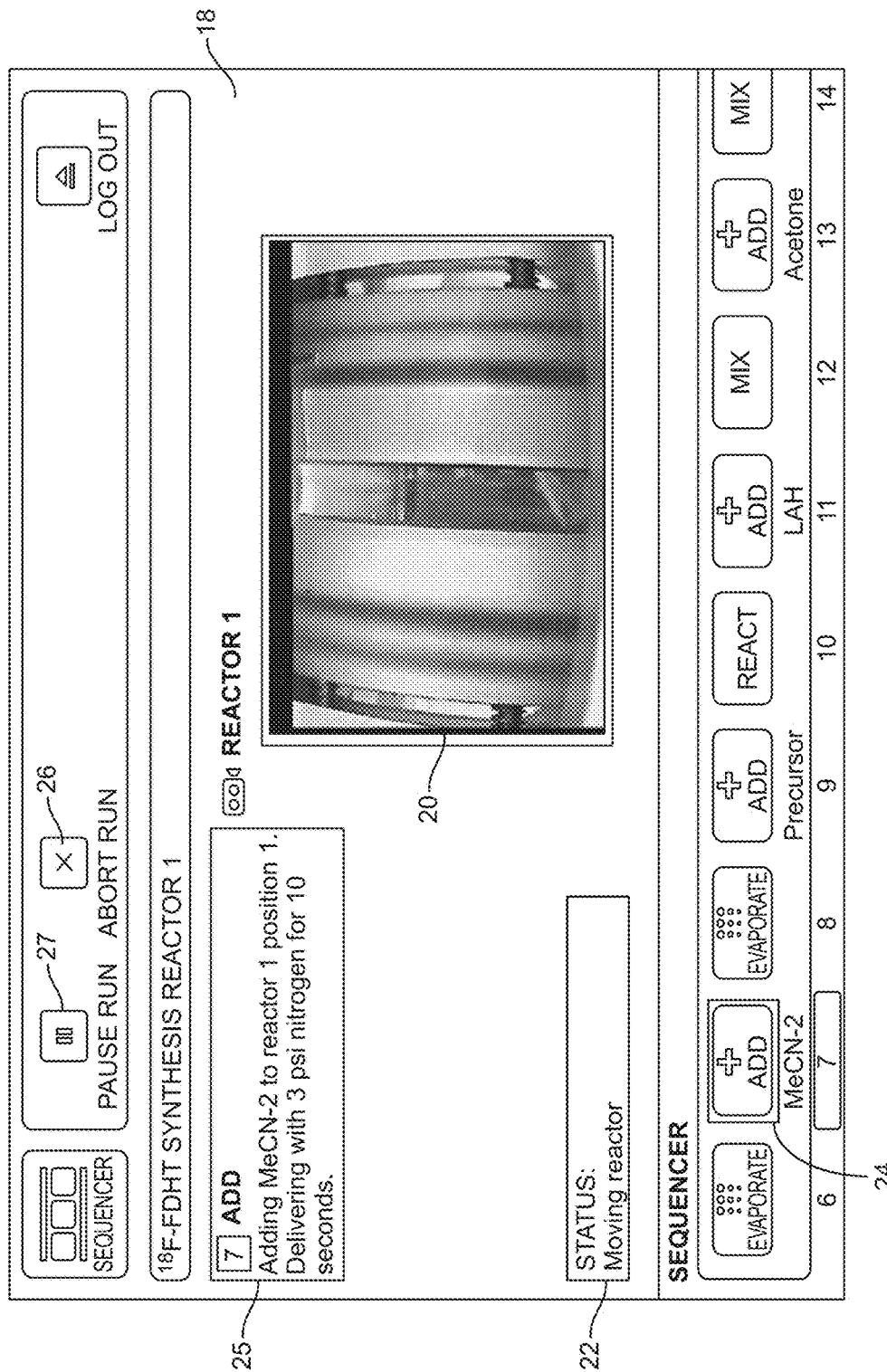
FIG. 3 illustrates an exemplary graphical user interface that can be displayed on a client device that displays relevant information as to the current unit operation occurring during a $^{18}$F-FDHT synthesis run.

FIG. 3 illustrates an exemplary display 18 that includes a graphical user interface can be displayed on a client device 16 that displays relevant information as to the current unit operation occurring during a synthesis run. In this particular example, $^{18}$F-FDHT is being synthesized and unit operation number seven (7) is currently being performed. The display 18 includes an active video 20 of reactor #1. The system status 22 indicates the current operation being conducted by the synthesizer 12 (e.g., moving reactor #1). A sequencer 24 lists the unit operations in the order in which they are to be performed. Unit operations are performed in a serial fashion moving from one unit operation to the next (left to right). The current unit operation 25 is highlighted as illustrated in FIG. 3 (e.g., ADD). The user may be permitted to abort a particular run using abort button 26. Likewise a user may temporarily pause a run using pause button 27.

Figure 4:
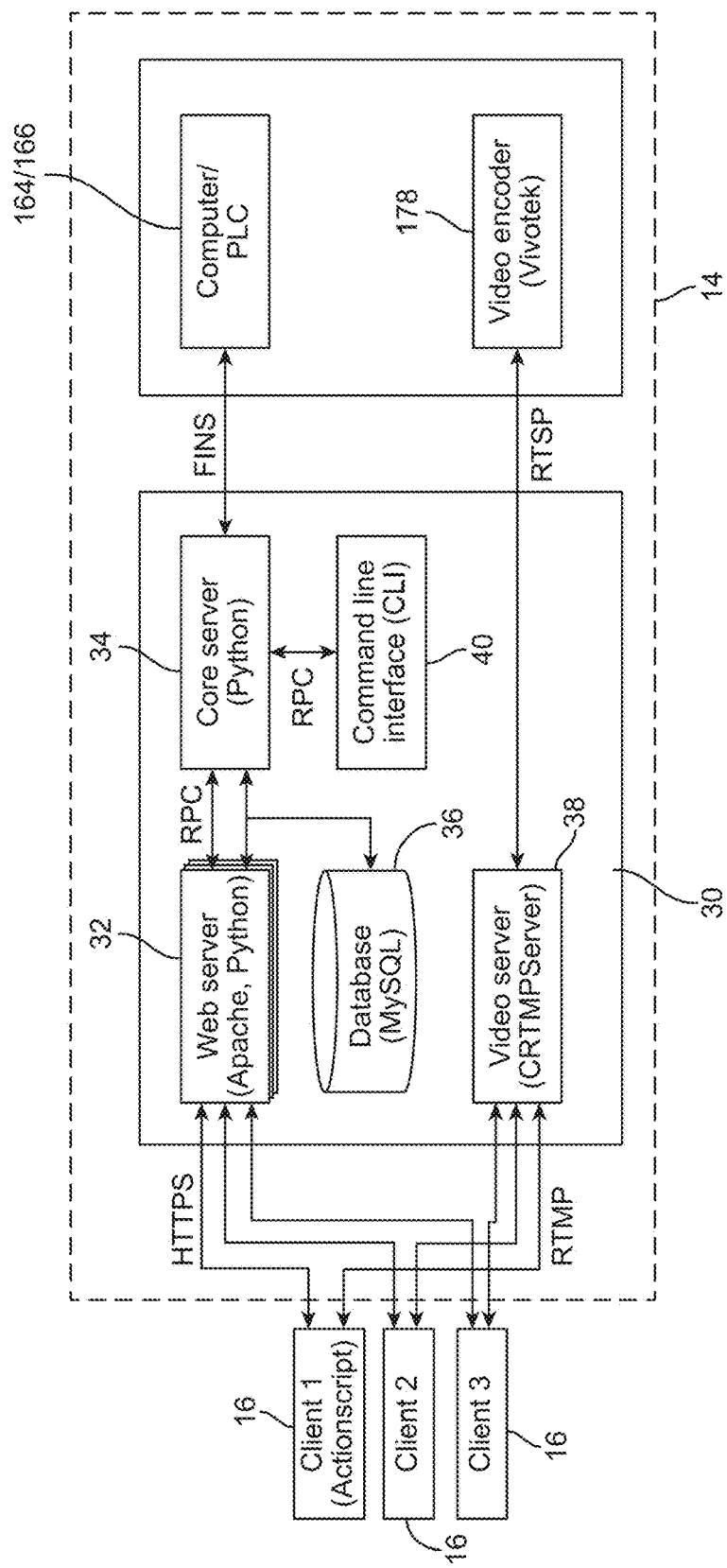
FIG. 4 illustrates an overview of the software architecture used as part of the interface between the client devices and the control system.

FIG. 4 illustrates an overview of the software architecture used as part of the interface between the client devices 16 and the control system 14 according to one embodiment. A server 30 interfaces with the client devices 16 using standard networking protocols to maximize the ability of client-server communication to pass through firewalls. Secure hypertext transfer protocol (HTTPS) is used to transmit all information with the exception of video which is sent using Adobe's real-time messaging protocol (RTMP). The server 30 is responsible for the actual execution of the synthesis program and is designed and built with maximum reliability in mind. To this end, open-source packages with known reliability can be used. Additionally, all information about the state of each client application is stored on the server, so nothing will be lost even if a critical failure (e.g., battery loss and software crash) occurs with the client device 16. The server 30 is driven by the client device 16 but acts independently once the production run has started to make the system resilient to intermittent network connectivity or failures of the client device 16. The server 30 is composed of five main applications. A first main application includes the Web Server 32. An Apache HTTP (Forest Hill, Md., USA) is responsible for all client communication except video. A module written in Python (Wilmington, Del., USA) handles viewing and editing programs and only communicates with the core server for operations related to production runs.

A second application includes a Core Server 34. An application written in Python runs on the Core Server 34 and is responsible for running a program and communicating with a computer 164 or programmable logic controller (PLC) 166 located in the radiosynthesizer 12 that monitors and controls the state of the hardware. The computer 164 or PLC 166 constitutes the third tier of the software. The core server code has been separated from the web server to remove the overhead of program viewing and editing and to insulate it from any failures that might occur while processing client requests. All communications between the web and core servers are accomplished using remote procedure calls.

A third application includes the database (MySQL) server 36. All synthesis programs and user information as well as the complete production run history are stored in a MySQL database (Redwood City, Calif., USA), a widely used, reliable, open-source relational database. A fourth application includes a video server 38 that is linked to a video encoder 178 to encode the analog signals from the reactor cameras 64 into video streams. Three live video feeds (one for each reactor) from the respective cameras 64 at each reactor assembly are generated by a hardware encoder 178 within the synthesizer 12 as real-time streaming protocol streams and are converted to the Flash-compatible format RTMP by C++ RTMP Server (e.g., EvoStream (San Diego, Calif., USA) and published for simultaneous consumption by multiple client devices.

A fourth application includes a command line interface 40. A terminal-based command line interface 40 provides a way to monitor the status of all hardware components and offers a mechanism to control the system directly at a low level. Although not needed by or intended for end users, this application is useful for software developers and maintenance technicians.

Figure 5B:
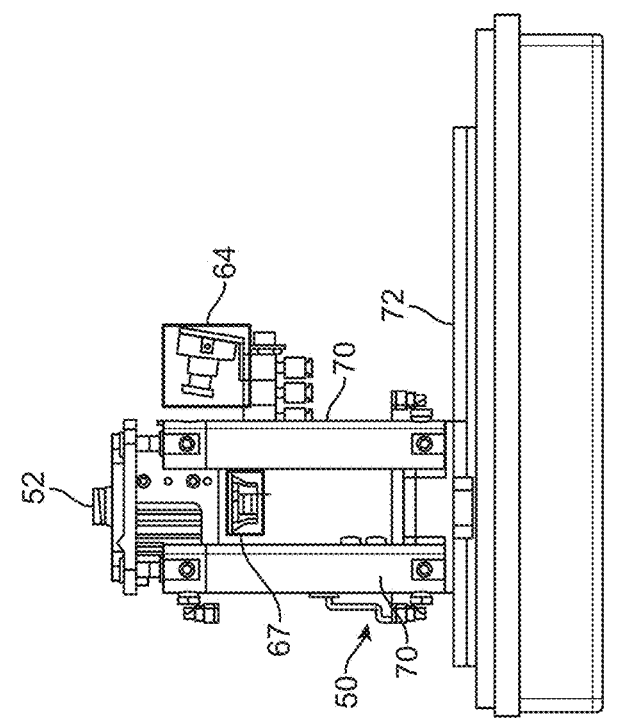
FIG. 5B illustrates a side view of the single reactor assembly of FIG. 5A.
Figure 5C:
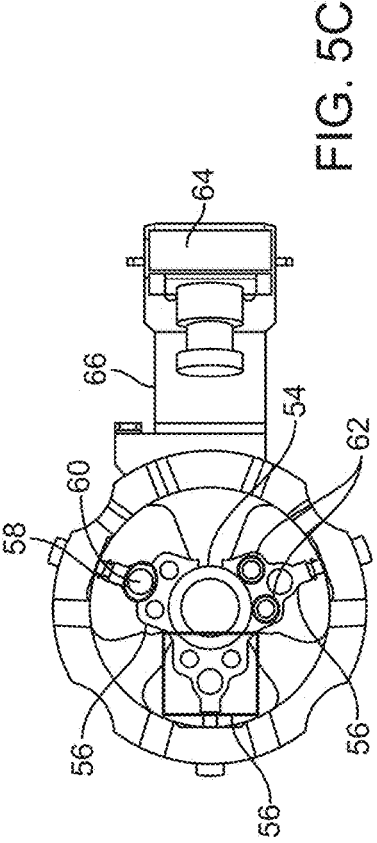
FIG. 5C illustrates a top down view of single reactor assembly illustrated in FIG. 5B.
Figure 5A:
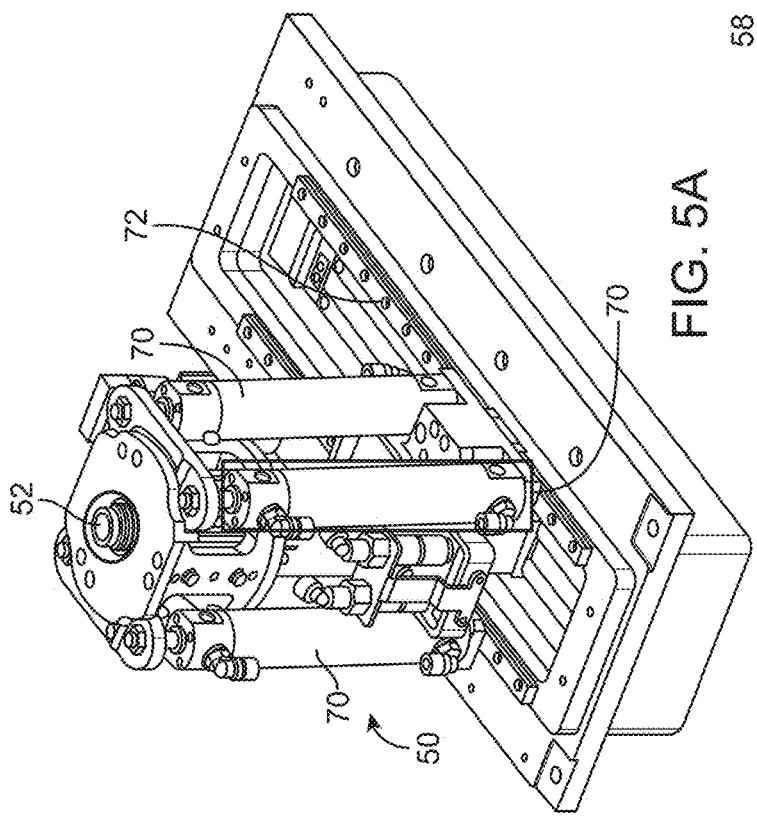
FIG. 5A illustrates a perspective view of a single reactor assembly contained within a horizontal actuator.

The automated synthesizer 12 includes several main subsystems that are used to carry out the various radiosynthesis operations. A first main subsystem includes a plurality of reactor assemblies 50 as seen in FIG. 2. The reactor assemblies 50 are used to hold a reactor vial 52 (e.g., 5 mL glass V-vial) within a central aperture 54 (as seen in FIGS. 5A, 5B, and 5C). Each reactor vial 52 is configured to hold reagents, precursors, and products generated during the radiosynthesis operations. In the illustrated embodiment of FIG. 2 there are three such reactor assemblies 50 (e.g., reactor #1, reactor #2, and reactor #3 from left to right in FIG. 2). While three such reactor assemblies 50 are illustrated, there could be more or less depending on the particular synthesis. Further, even in a configuration with three (3) reactor assemblies such as that illustrated, only one or two reactor assemblies 50 could be utilized in any particular run. In some embodiments, the reactor vial 52 is open at the upper lip or rim. In other embodiments, however, the reactor vial 52 may be sealed with a septum which is penetrated by needles located on the underside of cassettes 80.

Each reactor assembly 50 includes a plurality of spring-biased heating assemblies 56 (FIG. 5C). Three such spring-biased heating assemblies 56 are shown in FIG. 5C. The spring-biased heating assemblies 56 use respective springs to press the heating assembly radially inward against the surface of the reactor vial 52 when placed therein. In this regard, the spring-biased heating assemblies 56 act as a three-segment spring-loaded "chuck." Each spring-biased heating assembly 56 presses firmly against the reactor vial 52 to ensure excellent thermal contact and thus efficient heat exchange between the reactor assembly 50 and the reactor vial 52. Each spring-biased heating assembly 56 includes a 100 W cartridge heater 58 (CIR-1021-120V-100W-ST-A, Valin; San Jose, Calif., USA) and a K-type thermocouple 60 (HTTC72-K-116U-1.25-UNGR, Omega Engineering; Stamford, Conn., USA) for individual feedback control of the reactor assembly temperature up to 185° C. Since a very similar temperature response was typically observed in all three segments, the reactor assembly temperature at any given moment is considered equal to the average of the three temperature readings from the thermocouples. Active liquid cooling is achieved by pumping room temperature coolant (propylene/ethylene glycol and water mixture) through cooling channels 62 in all three reactors in series by a liquid pump (8030-863-236, Steam Brite; San Antonio, Tex., USA) and then through a radiator with three mm fans (HX-CU1403V, Frozen CPU; East Rochester, N.Y., USA) (not shown).

The reactor assembly 50 further includes a camera 64 (PC213XS, Super Circuits; Austin, Tex., USA) affixed to a mount 66. The camera 64 was mounted behind the reactor assembly 50, which is helpful for monitoring liquid levels during evaporations, to observe visual cues for reaction progression, to confirm reagent additions and transfers, and for visual inspection of the eluate post purification. The camera 64 is oriented relative to the spring-biased heating assembly 56 such that it has a clear view of the reactor vial 52. In one embodiment, as best seen in FIG. 5D, portions of the spring-biased heating assembly 56 may have optional graduation marks 57 in the form of collets to gauge liquid volume in the reactor vial 52 (visible to camera 64).

Figure 5D:
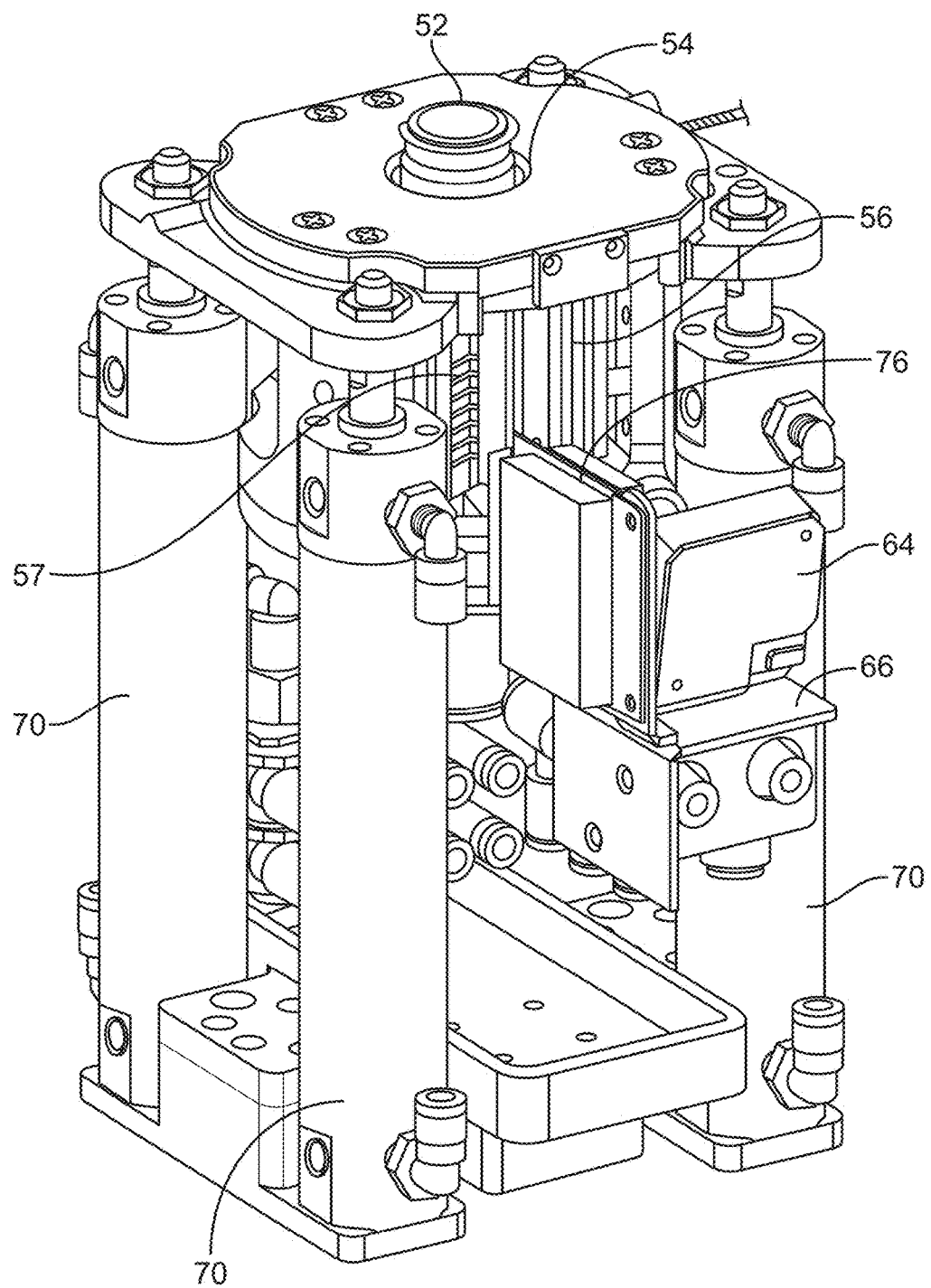
FIG. 5D illustrates a perspective view of a reactor assembly according to another embodiment illustrating the position of a radiation sensor.

Referring to FIGS. 5A, 5B, and 5D, each reactor assembly 50 includes a plurality of vertically-oriented actuators 70 that are mounted at one end (bottom) to a horizontally-oriented actuator 72. The opposing end of the vertically-oriented actuators are mounted to the reactor assembly 50 so that the entire reactor assembly 50 can be raised and lowered depending on actuation of the vertically-oriented actuators 70. In one aspect, there are four (4) such vertically-oriented actuators 70 with each actuator being a pneumatic actuator that is coupled to a source of valved, pressurized gas. When pressurized gas is delivered to the vertically-oriented actuators 70, the reactor assembly 50 is raised in the vertical direction so as to place the reactor vial 52 therein in a sealed configuration against gaskets 90 (FIG. 6C) positioned on the bottom surface of disposable cassettes 80 positioned directly above each reactor assembly 50 (described in more detail below). Also, as described above, the horizontally-oriented actuator 72 is able to move the reactor assembly 50 in the lateral direction. This two axis movement by the reactor assembly 50 permits the reactor vial 52 to be selectively and dynamically configured for different unit operations based on the particular gasket 90 that it interfaces with on the underside of the disposable cassette (described below).

For example, in one position, the gasket 90 is un-sealed within internal plumbing or fluid paths within a disposable cassette 80 configured to deliver reagents to the reactor vial 52 within the reactor assembly 50. In another position, the gasket 90 is sealed, allowing for a reaction under sealed conditions. Permanent tubing and valve connections to the reaction vessel are the root cause of the reaction pressure limitations of most synthesizers. The ability to move the reactor vial 52 to a dedicated sealed reaction position eliminates these limitations and enables compatibility with higher pressures. To ensure reliable operation, the position of the reactor assembly 50 is monitored via feedback from the linear actuator and the raised or lowered state is detected with Hall effect sensors (D-M9NWL, SMC Corporation; Noblesville, Ind., USA).

The horizontally-oriented actuators 72 which move, respectively, the reactor assemblies 50 in the y-axis may include linear servo motors (RCP3-SA3R-I-28P-4-200-P1-P-ML, IAI America Inc.) driven by linear servo motor controllers (RACON-5, IAI America Inc.). The y-axis movement of the horizontally-oriented actuators 72 is aligned with the direction of the gaskets aligned along the bottom of the disposable cassette (discussed below). The reactor assemblies 50 each include magnets mounted on a DC motor 67 as seen in FIG. 5B (803-313-5858, KALEJA Elektronik GmbH; Alfdorf, Germany) which interact with a removable magnetic star bar located inside the reaction vial 52, causing the magnetic stir bar to rotate for mixing operations. The reactor assemblies 50 each optionally include a radiation sensor (not shown) that is mounted adjacent to the camera 64. The radiation sensor may be mounted to the mount 66. An optional radiation sensor (not shown) may also be placed adjacent to a purification cartridge that is used during the synthesis to measure radioactivity levels.

With reference now to FIGS. 2 and 6A-6D, the synthesizer 12 includes a plurality of disposable cassettes 80 that can be manually loaded into the synthesizer 12 and affixed into place into respective bays 82 located vertically above each reactor assembly 50. Thus, in a "three-pot" reactor assembly 50 configuration, there are three bays 82 with each bay holding an individual cassette 80. The cassettes 80 store reagents in sealed vials 84 on an upper surface 86 in one of a plurality of vial storage positions 88, act as the primary fluid path for both reagents and gas flow, and have a rubber or silicone gasket 90a-90d (seen in FIG. 6C) affixed to a lower surface 92 of the cassette 80 for sealing the top or lip of the reaction vials 52 or for providing access to reagents, gases, and vacuum for various unit operations. The cassettes 80 accelerate setup and eliminate the need for cleaning, thus facilitating the transition from tracer development to routine production. The cassettes 80 can be made from molded polyurethane, tubing, chemically-inert three-way stopcock valves 102 (EW-31200-80, Cole-Parmer; Vernon Hills, Ill., USA), and a custom PTFE-coated silicone gasket 90 (Specialty Silicone Products, Inc.; Ballston Spa, New York, USA; and Cannon Gasket; Upland, Calif., USA) against which the reactor vial 52 is sealed.

Figure 6A:
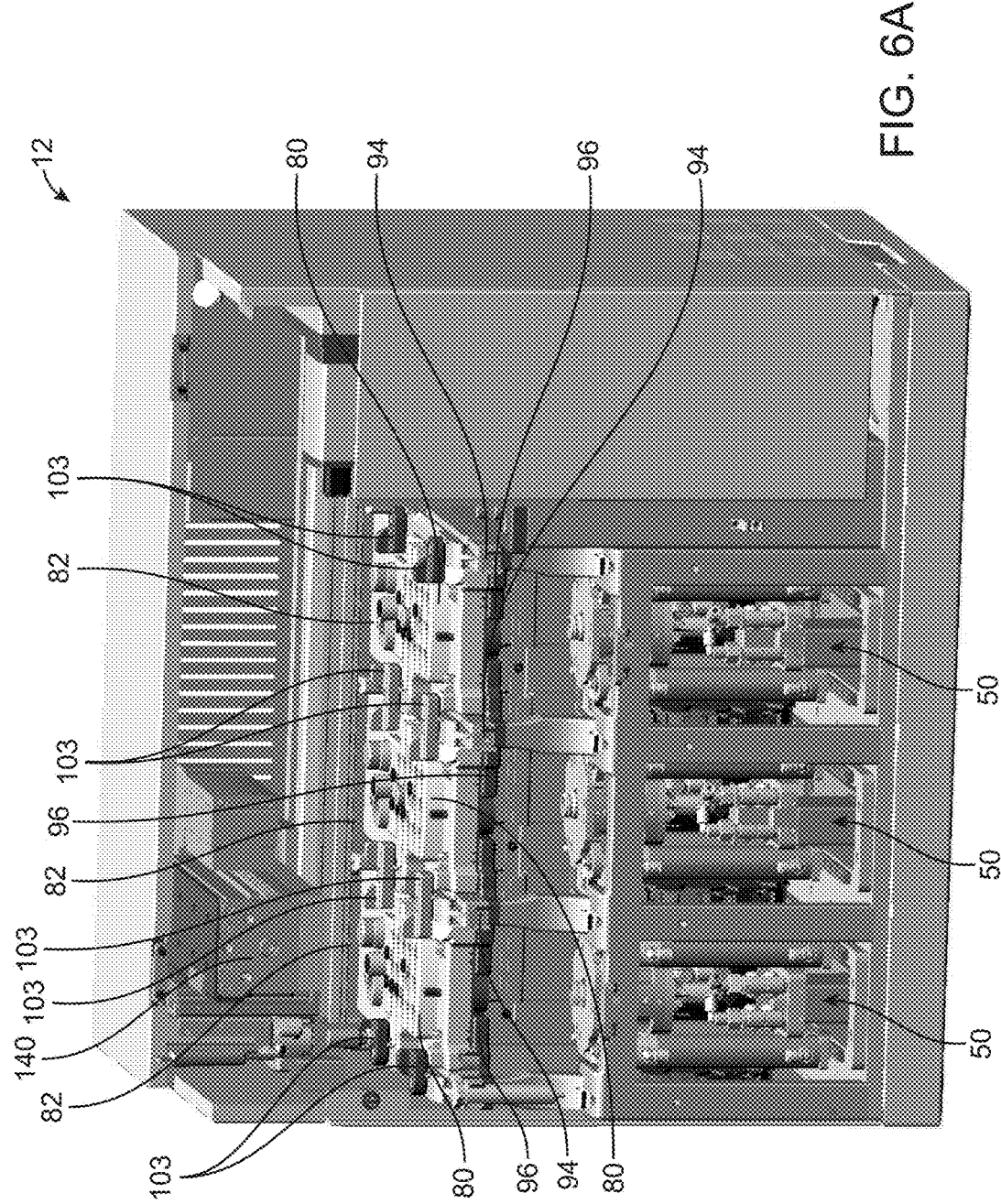
FIG. 6A illustrates a synthesizer according to one embodiment.

The cassettes 80 are manually loaded into each bay 82 using respective rails 94 that interface with tabs 95 located on the cassettes 80. Once the cassettes 80 are slid into the bays 82 sufficiently, they drop onto a support plate 96 that holds the cassettes 80. Each cassette 80 contains a plurality of alignment pegs 98 located in the bottom surface that engage with corresponding holes (not shown) in the support plate 96. The cassettes 80 are also held into position with adapters that are secured to three valve actuators that engage with three corresponding stopcock valves 102 that are accessible via the lower surface 92 of the cassette 80. The cassettes 80 can be further held in place using fasteners 103 which may take the form of rotatable clips or knobs (as seen in FIG. 6A).

Figure 6B:
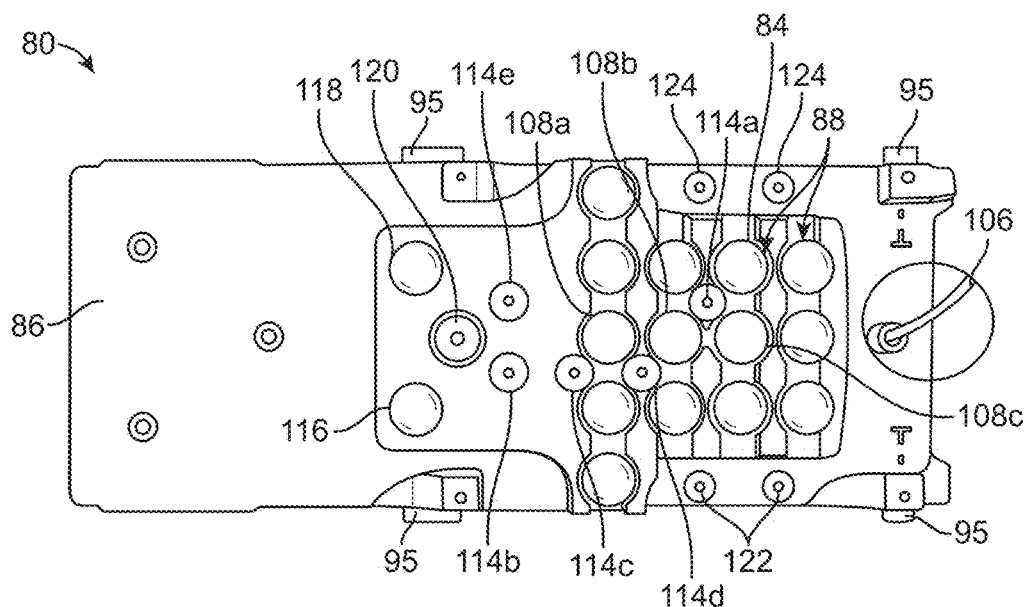
FIG. 6B illustrates a top down view of a disposable cassette according to one embodiment.
Figure 6C:
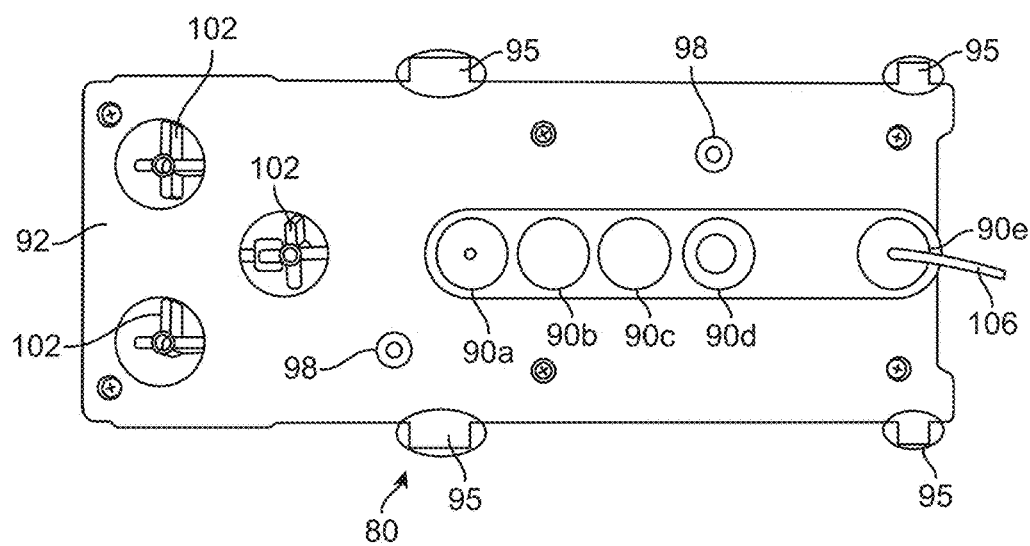
FIG. 6C illustrates a bottom up view of a disposable cassette according to one embodiment.
Figure 6D:
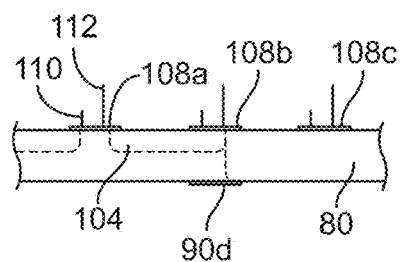
FIG. 6D illustrates a cross-sectional view of disposable cassette.

FIG. 6C illustrates a view of the bottom or lower surface 92 of the cassette 80. The three stopcock valves 102 are illustrated. As noted above, the stopcock valves 102 can be rotated using a valve actuator. The valve actuator is preferably a rotary pneumatic actuator that can turn between two states (CRB2BW20-1805, SMC Corporation). Also illustrated are a series of gaskets 90a, 90b, 90c, 90d, and 90e. Gaskets 90a, 90b, 90c, 90d, and 90e are formed from a rubber or silicone material and are dimensioned to encompass the full diameter of the upper lid or rim of the reactor vial 52. The gaskets 90a, 90b, 90c, 90d, and 90e may be formed from a single piece of rubber or silicone material with separate gasket locations being formed in the cassette 80. Gasket 90a is un-sealed in that an aperture is located in the gasket 90a and is in communication with an internal fluid path 104 of the cassette 80 (internal flow path 104 illustrated in FIG. 6D and FIGS. 7B-7G). Gasket 90a is used for the EVAPORATE unit process whereby vacuum is pulled in conjunction with flow of an inert gas. Gasket 90b and gasket 90c are sealed gaskets that do not have any aperture or other access into to the internal fluid path 104 of the cassette 80. These gaskets 90b, 90c are used for the REACT unit process whereby high pressures can be formed and maintained within the reactor vial 52 when the reactor assemblies are positioned below the same and actuated in the elevated position. Gasket 90d is un-sealed in that an aperture is located in the gasket 90d and is communication with an internal fluid path 104 within the cassette 80. Gasket 90e is an un-sealed gasket that includes a dip tube 106 that extends through the cassette 80 and is used extract fluid from a reactor vial 52. Fluid can be extracted by injecting inert gas into the reactor vial 52 through a needle or aperture passing through gasket 90e to push fluid into the dip tube 106. Fluid can then be transferred via the dip tube 106 to another cassette 80, for example. As noted above, in some embodiments, the lower surface 92 of the cassette 80 has needles or the like to penetrate sealed reactor vials 52. Such may be the case when the reagents used in the automated synthesizer 10 are air or moisture sensitive.

FIG. 6B illustrates top view of the cassette 80 illustrating the upper surface 86. The upper surface 86 includes a plurality of vial storage positions 88 that are used to store sealed storage vials 84 (also FIG. 7A) that contain reagent therein. FIG. 6B illustrates the reagent positions (#1-#12) for storage vials 84. The storage vials 84 are crimped septum-cap vials (e.g., 13 mm vials with maximum volume of 3 mL). Twelve (12) such storage vials 84 are illustrated being stored in the upside down configuration in the cassette 80 although more or less could be used. The cassette 80 also includes a plurality of reagent addition positions 108a, 108b, 108c. The reagent addition positions 108a, 108b, 108c are used in the ADD unit operation to add reagents to one of the reactor vials 52. Each reagent addition position 108a, 108b, 108c includes two upward pointing needles 110, 112 (FIG. 6D) that are used to pierce the septa in the storage vials 84 for fluid delivery to the internal fluid path 104 of the cassette 80 (e.g., stainless steel needles (Vita Needle; Needham, Mass., USA)). A shorter needle 110 in each addition position 108a, 108b, 108c is used for fluid delivery. The other needle 112, which is longer, connects to an inert gas port 114 (one of 114a-114e) on top of the cassette 80 which allows pressurization of the vial by the gas manifold. In the two reagent addition positions 108b, 108c, the fluid delivery needles 110, 112 output directly to the underside of the cassette 80 where the reaction vial 52 is sealed for reagent addition. The fluid delivery needle in the third position 108a (for eluent addition) is connected via an internal fluid path 104 to a stopcock valve 102.

Still referring to FIG. 6B, the cassette 80 includes a number of inlet gas ports 114a, 114b, 114c, 114d, 114e. Gas inlet port 114a is connected via an internal fluid path 104 to the dip tube 106. The gas inlet ports 114b, 114c, 114d are each respectively coupled to reagent addition positions 108a, 108b, 108c. Thus, each reagent addition position 108a, 108b, 108c has a dedicated gas inlet port 114b, 114c, 114d. Gas inlet port 114e is used to supply a stream of inert gas through the reactor vial when it is in the evaporate position. The cassette 80 further includes a cartridge waste vial location 116 that holds a vial that receives waste. The cassette 80 also includes a recovery vial location 118 that holds a vial that receives recovered [$^{18}$O]H$_2$O. The upper surface 86 of the cassette 80 further includes a vacuum port 120 that selectively interfaces with a gas manifold on the reagent and gas handling robot 140 (FIG. 6A) that is coupled to a source of vacuum. In this regard, vacuum can be supplied to the gasket 90a for the EVAPORATE unit operation. Additional details regarding the gas manifold and gas handling robot 140 may be found in published PCT Application No. WO 2014/160799, which is incorporated by reference herein.

The cassette 80 further includes inlet ports 122 that are used to deliver fluid into internal fluid path 104 of the cassette 80. Tubing is used to connect to the inlet ports 122 and can be used to deliver fluids into the cassette 80 (and ultimately the reactor vial 52) from an external source outside the cassette 80. Alternatively, the output of one cassette 80 may be input to another cassette 80 using the inlet ports 122. Likewise, outlet ports 124 are provided on the cassette 80 that are configured to connect to tubing. The outlet ports 124 may output a fluid that is collected at a collection vial 126 (FIG. 7A) for the final product. Alternatively, the outlet ports 124 can be used to transport an intermediate or precursor from one cassette 80 to another cassette 80. For example, tubing or other conduit may be connected between the outlet port 124 of a first cassette 80 and terminate at the inlet port 122 of another, separate cassette 80.

Figure 7A:
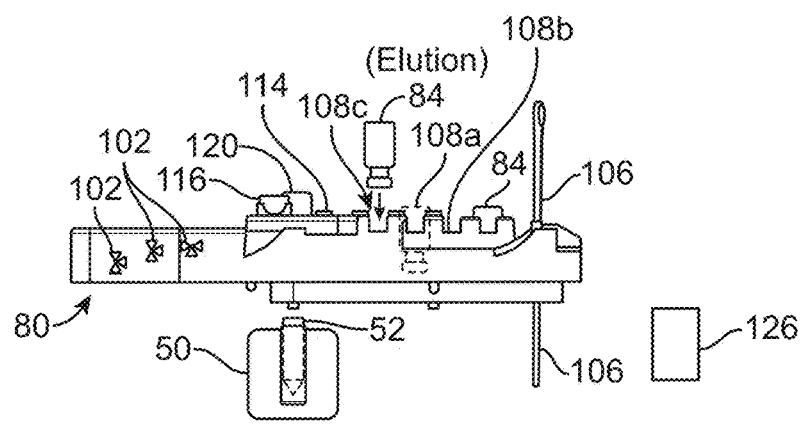
FIG. 7A illustrates a side profile schematic of the disposable cassette.
Figure 7B:
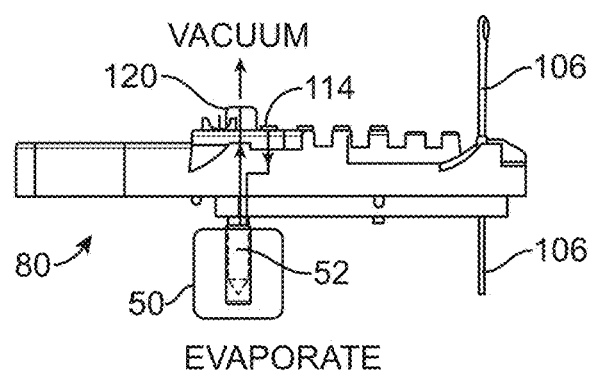
FIG. 7B is a schematic drawing showing the cassette fluid path for the EVAPORATE unit operation. Gas supplier provides vacuum and inert gas flow while reactor is heated.
Figure 7C:
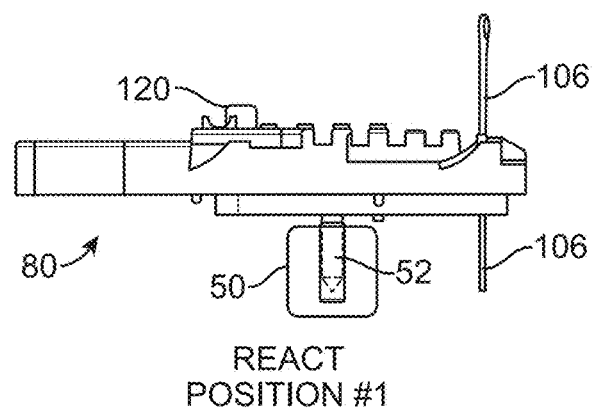
FIG. 7C is a schematic drawing showing the cassette fluid path for the REACTION unit operation. The reaction takes place at the first fully-sealed reaction position.
Figure 7D:
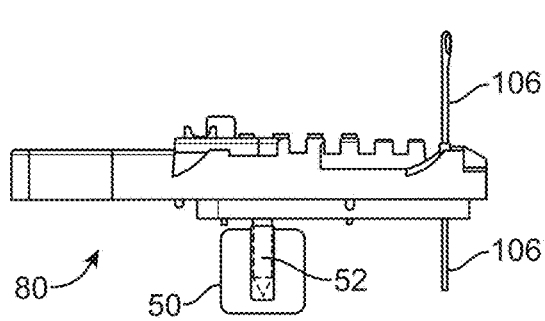
FIG. 7D is a schematic drawing showing the cassette fluid path for the REACTION unit operation. The reaction takes place at the second fully-sealed reaction position.

FIG. 7A illustrates a side profile schematic representation of the cassette 80. The three (3) stopcock valves 102 can be seen. A reactor assembly 50 containing a reactor vial 52 is illustrated below gasket 90a used for the EVAPORATE unit process. FIG. 7B illustrates a side profile view of the cassette 80 illustrating the gas flow path 128 and the vacuum flow path 130. The reactor assembly 50 is in the raised position so as to place the reactor vial 52 against the gasket 90a for the EVAPORATE unit process to take place. FIGS. 7C and 7D illustrate the reactor assembly 50 in react positions #1 and #2 for REACT unit processes to take place. FIG. 7C illustrates the reactor assembly 50 in the raised position so as to place the lip or rim of the reactor vial 52 against the sealed gasket 90b. FIG. 7C illustrates the reactor assembly 50 in the raised position so as to place the lip or rim of the reactor vial 52 against the sealed gasket 90c. In this position, high temperature and high pressure reactions can take place within the reactor vial 52.

Figure 7E:
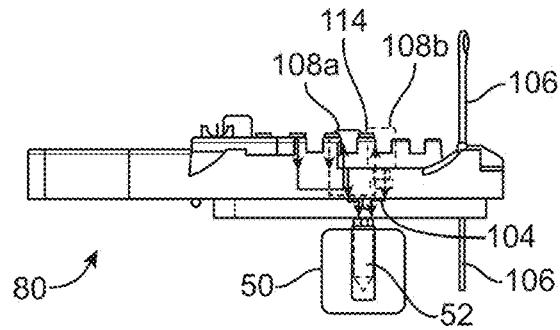
FIG. 7E is a schematic drawing showing the cassette fluid path for the ADDITION unit operation. Vial gripper presses a reagent vial into one of two addition positions where two needles pierce the vial's septum; one needle allows inert gas flow from the gas supplier through the inert gas port and the other needle allows the reagent to flow into the reaction vessel.
Figure 7F:
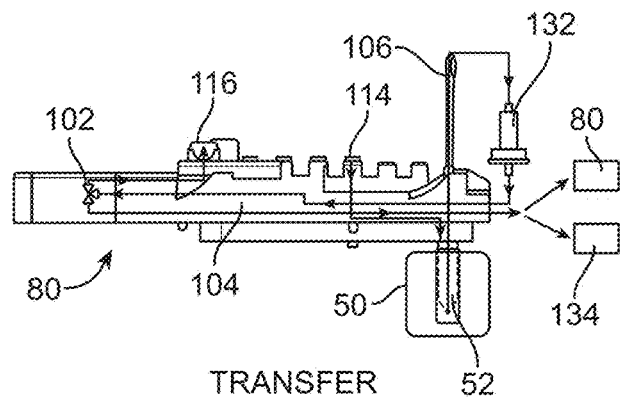
FIG. 7F is a schematic drawing showing the cassette fluid path for the TRANSFER unit operation. The contents of one reaction vessel are transferred to another cassette, the HPLC valve, or to a purification cartridge.

FIG. 7E illustrates a configuration whereby the reactor assembly 50 and the reactor vial 52 contained therein are placed in the addition position for the ADD unit operation. Here, the reactor assembly 50 is in the raised position so as to place the lip or rim of the reactor vial 52 against the un-sealed gasket 90d. Reagents can then be actively transported into the reactor vial 52 via the internal fluid path 104 by flowing inert gas through inert gas port 114 to displace the reagent from the storage vial 84 and into reactor vial 52. FIG. 7F illustrates configuration whereby the reactor assembly 50 and the reactor vial 52 contained therein are placed in transfer position for the TRANSFER or TRANSFER TO HPLC unit operations. The reactor assembly 50 is in the raised position so as to place the lip or rim of the reactor vial 52 against the un-sealed gasket 90e. The dip tube 106 is used to transfer the fluid contained within the reactor vial 52 to another location. Such a location could include another cassette 80, a purification cartridge 132 as illustrated, or a HPLC injection valve 134, or a collection vial 126 to store a final product. FIG. 7F illustrates a purification cartridge 132 that is coupled to the output of the dip tube 106.

The purification cartridge 132 is installed between the dip tube 106 (for removal of crude product from the reaction vial 52) and the tube leading to the stopcock valve 102. The outputs of the stopcock valve 102 are connected to a built-in waste vial 116 (trapping, washing) or an external output line via outlet port 124 (release). Cartridges 132 can optionally be mounted on clips near the front of the cassettes 80 for convenience. Alternatively, the cartridges 132 can be mounted on a support structure of the synthesizer 12 separate from the cassettes 80.

Figure 7G:
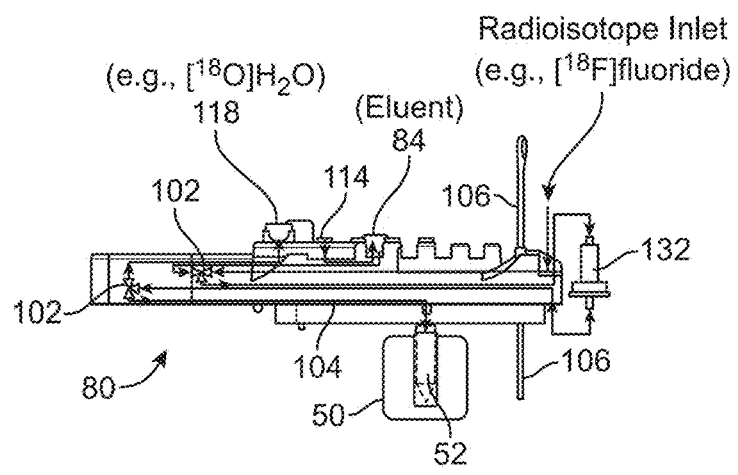
FIG. 7G is a schematic drawing showing the cassette fluid path for the Radioisotope handling ADDITION unit operation. $^{18}$F-fluoride trap and release is performed using two of the built in stopcock valves.

FIG. 7G illustrates a configuration used for radioisotope handling. In this configuration, [$^{18}$F]fluoride trap and release can be done using two of the built in stopcock valves 102. The reactor assembly 50 and reactor vial 52 are raised to contact the upper lip or rim of the reactor vial to the un-sealed gasket 90d. Radioisotope such as [$^{18}$F]fluoride obtained from a cyclotron or vial is input into the cassette 80 via the inlet tubing port. In nucleophilic fluorine-18 radiochemistry, [$^{18}$F]fluoride is trapped on a strong anion exchange resin such as quaternary methylammonium (QMA) resin for purification and recovery of [$^{18}$O]H$_2$O and released in a solution with lower water content to reduce the time needed for drying. This is accomplished using a cassette 80 that is coupled to a QMA cartridge 132 via Luer fittings between tubes coming from the cassette 80. If an external vial is used, an external inert gas delivery line coupled to an inert gas port 114 is available to pressurize the vial for delivery on demand. Alternatively, the gas delivery system of the cyclotron can be used to directly push the [$^{18}$F]fluoride into the system. In FIG. 7G, this flow is valved using stopcock valve 102 to a purification the QMA cartridge 132. During trapping, the [$^{18}$F]fluoride source solution flows through the QMA cartridge 132 where [$^{18}$F] fluoride is retained and the carrier [$^{18}$O]H$_2$O, then flows into the recovery vial 118 in the cassette 80. During elution, stopcock valve 102 positions are switched and the gas handling robot drives the eluent from the eluent addition position of the cassette 80 through the QMA cartridge 132 and into the reactor vial 52. Multiple elutions can be performed to increase efficiency of [$^{18}$F]fluoride collection. PEEK tubing can be used for all fluid paths involving [$^{18}$F]fluoride to maximize specific activity. For other radioisotopes, a cartridge 80 may not be necessary and can be bypassed. Radioisotopes may be added to any of the three reactors independently. While the synthesis process has been described in the context of one embodiment of the ELIXYS radiosynthesizer platform it should be understood that the method is applicable other iterations and improvements to the ELIXYS radiosynthesizer platform as well as other commercial radiosynthesizer platforms.

Cassette Setup

The synthesis of $^{18}$F-FDHT was performed using two reactors and two cassettes. Reactor 1 was used for all reaction and evaporation steps, and all reagents were loaded into Cassette 1 (Table 1 below).

TABLE 1

List of reagents as organized on Cassette #1.

| Position | Reagent |
|---|---|
| 1 | 6.5 µL of ~40% TBAH (aq) with 0.5 mL water and 0.5 mL MeCN |
| 2 | 1.0 mL MeCN (MeCN-1) |
| 3 | 1.0 mL MeCN (MeCN-2) |
| 4 | 8.0 mg precursor in 0.5 mL THF |
| 5 | 0.35 mL of 1.0M LiAlH$_4$ in diethyl ether |
| 6 | 0.10 mL acetone in 0.25 mL THF |
| 7 | 1.0 mL of 3.0N HCl |
| 8 | 3.0 mL of water (Water-1) |
| 9 | 3.0 mL of water (Water-1) |
| 10 | 3.0 mL of water (Water-1) |
| 11 | 2.5 mL DCM (DCM-1) |
| 12 | 2.5 mL DCM (DCM-2) |

Figure 8:
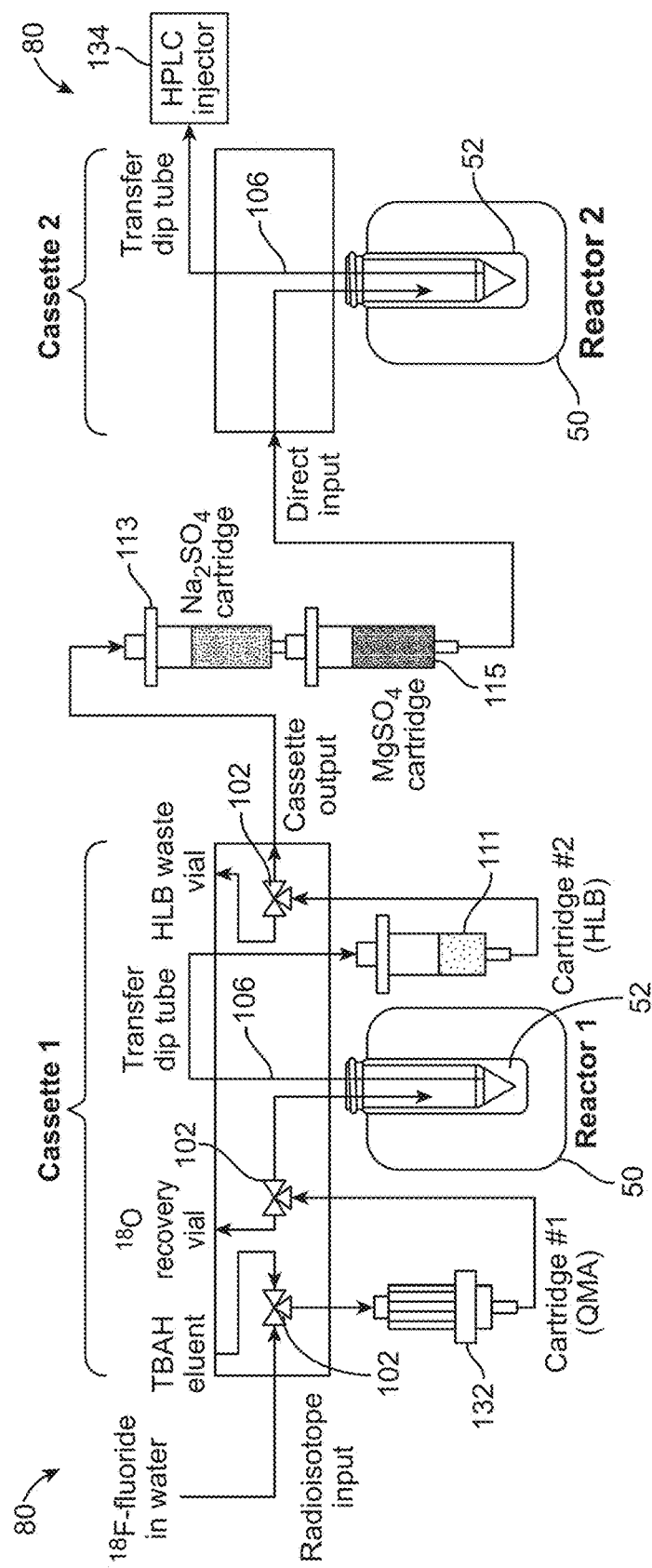
FIG. 8 illustrates the fluid flowpaths used in the synthesis of $^{18}$F-FDHT using the ELIXYS radiosynthesizer according to one embodiment.

The $^{18}$F-fluoride source vial was connected to the radioisotope input of Cassette 1, and a QMA cartridge 132 was installed in Cartridge Position #1. A hydrophilic-lipophilic balanced (HLB) cartridge 111 was installed in Cartridge Position #2 for solid-phase extraction prior to HPLC purification. The output of the pathway from the HLB cartridge 111 was connected to a Na$_2$SO$_4$ cartridge 113, followed by a MgSO$_4$ cartridge 115, and finally to the direct-input of Cassette 2. In this embodiment, Cassette 2 was used simply to load the crude product into the HPLC loop for purification. An illustration of the fluid flow path diagram is shown in FIG. 8.

In an alternative embodiment, the drying cartridges (i.e., Na$_2$SO$_4$ cartridge 113 and MgSO$_4$ cartridge 115) may be omitted entirely. In this alternative embodiment, normal-phase HPLC is used instead of a reverse-phase HPLC. The sequence of unit operations in accordance with this embodiment may be found in Table 5 below.

Materials

No-carrier-added $^{18}$F-fluoride was produced by the (p, n) reaction of $^{18}$O—H$_2$O (84% isotopic purity, Medical Isotopes; Pelham, N.H., USA) in a RDS-112 cyclotron (Siemens; Knoxville, Tenn., USA) at 11 MeV using a 1 mL tantalum target with Havar® foil. All commercially available reagents were used as received unless otherwise specified. Anhydrous solvents were obtained by filtration through activated alumina columns. Sodium sulfate anhydrous (Na$_2$SO$_4$; granular, EMD Chemicals), magnesium sulfate anhydrous crystalline (MgSO$_4$; MP Biomedicals) and HPLC grade dichloromethane (DCM) were obtained from Fisher Scientific (Pittsburgh, Pa., USA). HPLC grade ethyl acetate (EtOAc), HPLC grade acetonitrile (MeCN), anhydrous hexane, 1.0 M LiAlH$_4$ in diethyl ether, and tetrabutylammonium hydroxide (~40% in water) were obtained from Sigma-Aldrich (Milwaukee, Wis., USA). USP grade sterile saline was obtained from Hospira, Inc. (Lake Forest, Ill., USA). 200-proof ethanol (EtOH) was purchased from the UCLA Chemistry Department (Los Angeles, Calif., USA). FDHT precursor and cold standard were prepared as previously described by Liu et al. (1992b) at the MSKCC Organic Synthesis Core. The precursor solution used in each synthesis contained 8 mg of the precursor dissolved in 0.5 mL of anhydrous THF. LiAlH$_4$ solution was loaded into a reagent vial under an inert atmosphere of nitrogen in an mBraun UNILAB glovebox (Stratham, N.H., USA). All water used was purified to 18 MΩ and passed through a 0.1 mm filter.

Cartridges

HLB cartridges were purchased from Waters (Milford, Mass., USA) and preconditioned with 5.0 mL of EtOH, 10.0 mL of water, and dried with nitrogen. Preconditioned quaternary methylammonium (QMA) cartridges were purchased from ABX (K-920, Advanced Biochemical Compounds; Radeberg, Germany) and used as received. Drying cartridges were made in-house by filling empty polypropylene solid-phase extraction tubes, fitted with polypropylene frits (57024, Sigma-Adrich; Milwaukee, Wis., USA; 20 mm pore size), with either 2.0 g of Na2SO4 or 2.0 g of MgSO4 and capped with syringe adapters (210705, Grace; Columbia, Md., USA). For each synthesis, one of each cartridge was used. Sterile syringe filters (PVDF membrane) were purchased from Fisher Scientific (SLGVM33RS, 0.22 mm pore size, 33 mm diameter) and used for the final reformulation.

Chromatography

Semi-preparative HPLC (10 mL/min flow rate of 7% EtOAc in DCM) was performed with a WellChrom K-501 HPLC pump (Knauer; Berlin, Germany), normal-phase Luna column (5 mm, 21.2×100 mm$^2$, Phenomenex), ultra-violet (UV) detector (254 nm, WellChrom Spectro-Photometer K-2501, Knauer), and gamma-radiation detector and counter (B-FC-3300 and B-FC-1000; Bioscan Inc.; Washington, D.C., USA). Analytical HPLC (1 mL/min flow rate of 55% MeCN in water) was performed on a Knauer Smartline HPLC system with a Phenomenex reverse-phase Gemini column (5 mm, 4.6×250 mm$^2$) with inline Knauer UV (190 nm) and gamma-radiation coincidence detector and counter (B-FC-4100 and B-FC-1000). HPLC chromatograms were collected by a GinaStar (Raytest USA, Inc.; Wilmington, N.C., USA) analog to digital converter and GinaStar software (Raytest USA, Inc.) running on a PC. Specific activity values were determined by dividing the activity amount injected into analytical HPLC by the injected mass as calculated from a standard curve using $^{19}$F-FDHT. Radio-thin-layer chromatography (radio-TLC) was performed on a miniGita Star (Raytest USA, Inc.) using precut silica plates (Baker-flex; J. T. Baker) developed in 10% EtOAc in hexane (v/v). Samples taken for radio-TLC after LiAlH$_4$ reduction were immediately quenched in acetone prior to development and analysis.

Radiosynthesizer

Synthesis was performed using an ELIXYS automated radiosynthesizer at the Crump Cyclotron and Radiochemistry Technology Center in the Crump Institute of Molecular Imaging at UCLA. Details regarding the ELIXYS automated radiosynthesizer may be found in published PCT Application No. WO 2014/160799, which is incorporated by reference herein.

Synthesis Protocol

A vial containing the $^{18}$F-fluoride in water was connected via a dedicated transfer line to the first cassette (i.e., Cassette 1) on the ELIXYS using positive pressure (6 psig) through the QMA cartridge (see e.g., FIGS. 7G and 8 loading process). Trapped $^{18}$F-fluoride was subsequently eluted with tetrabutylammonium hydroxide (TBAH) eluent solution (Reagent Position #1, Table 1) into Reactor 1. Contents were partially evaporated while applying both vacuum and a stream of nitrogen (10 psig) at 110° C. for 4 min without stirring. Acetonitrile (Reagent Position #2) was added through the QMA ion exchange cartridge (3 psig driving pressure) to wash any remaining activity into Reactor 1, and the combined contents of Reactor 1 were similarly evaporated for 2 min. Acetonitrile (Reagent Position #3) was then directly added to Reactor 1, and the contents were fully evaporated using previous conditions for 2 min. Reactor 1 was then cooled to 30° C., and the precursor solution (Reagent Position #4) was then added. Contents were reacted at 75° C. for 5 min with stirring. Once the reaction was complete, the solution was cooled to room temperature, and the LiAlH$_4$ solution (Reagent Position #5) was slowly added (1 psig driving pressure), followed by 20 s of stirring. The synthesizer was set at the lowest driving pressure to deliver the LiAlH$_4$ solution in a slow manner (e.g., either a trickle or dropwise addition). The reduction reaction was quenched via the slow addition (1 psig driving pressure) of an acetone-THF solution (Reagent Position #6), and the solution was stirred for another 20 s. For both LiAlH$_4$ addition and addition of the acetone-THF solution the vial is pressed against the gasket on the underside of the cassette for a sealed reaction. Again, the acetone-THF solution was delivered at the lowest driving pressure to ensure a slow trickle flow (dropwise could also be used). HCl (Reagent Position #7) was added, and the solution was reacted at 75° C. for 10 min with stirring (with vial closed against gasket of cassette). Reactor 1 was cooled, and the contents were diluted with water (Reagent Position #8). The contents were transferred through the HLB cartridge (5 psig driving pressure), where the product was trapped and highly polar components such as $^{18}$F-fluoride passed through to a waste vial via a waste line. Reactor 1 and the HLB cartridge were rinsed with two more volumes of water (Reagent Positions #9 and #10; 5 psig driving pressure). The HLB cartridge was dried with nitrogen at 15 psig for 1.5 min. Reactor 1 was filled with dichloromethane (DCM) (Reagent Position #11), which was transferred through the HLB cartridge (10 psig driving pressure) and subsequently through the Na$_2$SO$_4$ and MgSO$_4$ cartridges; this process elutes the $^{18}$F-FDHT from the HLB cartridge and removes residual water before delivering the dry contents into a vial in Reactor 2. This process was repeated once more with DCM (Reagent Position #12), followed by the application of 15 psig of nitrogen gas for 45 s to ensure all liquid was transferred to Reactor 2. The $^{18}$F-FDHT product was purified by HPLC by remotely loading the crude solution into the HPLC loop provided on the ELIXYS and injecting the contents into the HPLC (Table 2).

Table 2 illustrates the reagent positions of Cassette #1.

| Tracer: FDHT FDHT ELIXYS PROTOCOL Cassette: 1 | | |
|---|---|---|
| Reagent Position | Reagent Name | Reagent Description |
| 1 | Eluent | 6.5 µL of ~40% TBAH (aq) in 0.5 mL water, 0.5 mL MeCN |
| 2 | MeCN-1 | 1.0 mL |
| 3 | MeCN-2 | 1.0 mL |
| 4 | Precursor | 8 mg in 0.5 mL THF |
| 5 | LiAlH$_4$ | 0.35 mL of 1M in ether |
| 6 | Acetone | 0.10 mL in 0.25 mL THF |
| 7 | HCl | 1 mL of 3N |
| 8 | Water-1 | 3 mL to wash |
| 9 | Water-2 | 3 mL to wash |
| 10 | Water-3 | 3 mL to wash |
| 11 | DCM-1 | 2.5 mL of DCM |
| 12 | DCM-2 | 2.5 mL of DCM |
| Sep-Pak A | QMA | Use ABX preconditioned ones to start |
| Sep-Pak B | HLB | Conditioned with 5 mL EtOH then 10 mL water |
| Waste A | O-18 Recovery | |
| Waste B | HLB Waste | Connected on output to cassette 2 is 1 × 2.0 g NaSO$_4$ then 1 × 2.0 g MgSO$_4$ cartridges (optional and may be omitted), waste must handle at least 20 mL |
| Elute F-18? | Yes | |
| Use Elute Position? | Yes | |
| Use Add Position 1? | Yes | |
| Use Add Position 2? | Yes | |
| Access HPLC? | No | |

Table 3 below indicates how the cassette #2 is used as a "dummy" cassette for the purposes of transferring fluid from cassette #1 and into the HPLC loop.

Table 2 illustrates the reagent positions/configurations of Cassette #2

| Tracer: FDHT FDHT ELIXYS PROTOCOL Cassette: 2 | | |
|---|---|---|
| Reagent Position | Reagent Name | Reagent Description |
| 1 | N/A | |
| 2 | N/A | |
| 3 | N/A | |
| 4 | N/A | |
| 5 | N/A | |
| 6 | N/A | |
| 7 | N/A | |
| 8 | N/A | |
| 9 | N/A | |
| 10 | N/A | |
| 11 | N/A | |
| 12 | N/A | |

-continued

Tracer: FDHT
FDHT ELIXYS PROTOCOL
Cassette: 2

| Reagent Position | Reagent Name | Reagent Description |
|---|---|---|
| Sep-Pak A | N/A | |
| Sep-Pak B | N/A | |
| Waste A | N/A | |
| Waste B | N/A | |
| Elute F-18? | No | |
| Use Elute Position? | No | |
| Use Add Position 1? | No | |
| Use Add Position 2? | No | |
| Access HPLC? | Yes | |

Table 4 illustrates the sequence of unit operations carried out the by the control system 14 for the automated synthesis of 16β-$^{18}$F-fluoro-5α-dihydrotestosterone ($^{18}$F-FDHT). Each unit operation is listed in chronological order according to the sequence of steps performed in the synthesis process.

TABLE 4

| Unit Operation | Reactor/Source | Reagent/Mode/Stir | Position/Target | Duration (s) | Temp (° C.) | Pressure (psig) |
|---|---|---|---|---|---|---|
| Initialize | | | | | | |
| Trap F18 | 1 | Trap | | 120 | | 6 |
| Elute F18 | 1 | Eluent | | 90 | | 3 |
| Evaporate | 1 | Off | | 240 | 110 | 10 |
| EluteF18 | 1 | MeCN-1 | 1 | 70 | | 4 |
| Evaporate | 1 | Off | | 120 | 110 | 10 |
| Add | 1 | MeCN-2 | 1 | 10 | | 3 |
| Evaporate | 1 | Off | | 120 | 110 | 10 |
| Add | 1 | Precursor | 1 | 10 | | 3 |
| React | 1 | On | 1 | 300 | 75 | |
| Add | 1 | LiAlH4 | 1 | 15 | | 1 |
| Mix | 1 | On | 1 | 20 | | |
| Add | 1 | Acetone | 1 | 20 | | 1 |
| Mix | 1 | On | 1 | 20 | | |
| Add | 1 | HCl | 1 | 15 | | 1 |
| React | 1 | On | 1 | 600 | 75 | |
| Add | 1 | Water-1 | 2 | 15 | | 5 |
| Transfer | 1 | Trap | 2 | 45 | | 5 |
| Add | 1 | Water-2 | 2 | 15 | | 5 |
| Transfer | 1 | Trap | 2 | 45 | | 5 |
| Add | 1 | Water-3 | 2 | 15 | | 5 |
| Transfer | 1 | Trap | 2 | 45 | | 5 |
| Transfer | 1 | Trap | 2 | 90 | | 15 |
| Add | 1 | DCM-1 | 1 | 25 | | 5 |
| Transfer | 1 | Elute | 2 | 90 | | 10 |
| Add | 1 | DCM-2 | 1 | 25 | | 5 |
| Transfer | 1 | Elute | 2 | 90 | | 10 |
| Transfer | 1 | Elute | 2 | 45 | | 15 |
| Move | 2 | | Transfer | | | |
| Run HPLC | | | | | | |

TABLE 5

| Unit Operation | Reactor/Source | Reagent/Mode/Stir | Position/Target | Duration (s) | Temp (° C.) | Pressure (psig) |
|---|---|---|---|---|---|---|
| Initialize | | | | | | |
| Trap F18 | 1 | Trap | | 120 | | 5 |
| Elute F18 | 1 | Eluent | | 90 | | 3 |
| Evaporate | 1 | Off | | 240 | 110 | 5 |
| EluteF18 | 1 | MeCN-1 | 1 | 90 | | 3 |
| Evaporate | 1 | Off | | 90 | 110 | 5 |
| Add | 1 | MeCN-2 | 1 | 15 | | 3 |
| Evaporate | 1 | Off | | 120 | 110 | 5 |
| Add | 1 | Precursor | 1 | 15 | | 3 |

TABLE 5-continued

| Unit Operation | Reactor/Source | Reagent/Mode/Stir | Position/Target | Duration (s) | Temp (° C.) | Pressure (psig) |
|---|---|---|---|---|---|---|
| React | 1 | On | 1 | 300 | 75 | |
| Add | 1 | LiAlH4 | 1 | 15 | | 1 |
| Mix | 1 | On | 1 | 20 | | |
| Add | 1 | Acetone | 1 | 15 | | 1 |
| Mix | 1 | On | 1 | 20 | | |
| Add | 1 | HCl | 1 | 15 | | 1 |
| Mix | 1 | On | 1 | 200 | | |
| Add | 1 | Water-1 | 2 | 15 | | 3 |
| Transfer | 1 | Trap | 2 | 45 | | 5 |
| Add | 1 | Water-2 | 2 | 15 | | 3 |
| Transfer | 1 | Trap | 2 | 45 | | 5 |
| Add | 1 | Water-3 | 2 | 15 | | 3 |
| Transfer | 1 | Trap | 2 | 45 | | 5 |
| Transfer | 1 | Trap | 2 | 90 | | 15 |
| Add | 1 | DCM-1 | 1 | 15 | | 3 |
| Transfer | 1 | Elute | 2 | 90 | | 10 |
| Add | 1 | DCM-2 | 1 | 15 | | 3 |
| Transfer | 1 | Elute | 1 | 90 | | 10 |
| Transfer | 1 | Elute | 1 | 45 | | 15 |
| Move | 2 | Activity Meas. | 2 | | | |
| Transfer | 2 | | Output-HPLC | | | 1 |

Reformulation

The final product was formulated in a ~8% ethanol in sterile saline solution. A remote-controlled fraction collector delivered the purified fraction of $^{18}$F-FDHT into a custom rotary evaporator fitted with a 100 mL glass pear flask. Contents were fully evaporated, dissolved with 0.5 mL of EtOH, and diluted with 6.0 mL of sterile saline. The final formulation was remotely transferred into a sterile vial through a 0.22 μm sterile filter.

Note that in an alternative embodiment, the rotary evaporator may be omitted entirely and reformulation may be done using a solid phase extraction (SPE) cartridge (e.g., Waters C19 Light cartridge). In this case, product coming of the HPLC column is diluted in water. The water dilution will allow the concentration of organic solvent to be low enough to effectively trap the desired product on the cartridge. The diluted can be pushed into and eluted from the SPE cartridge using a series of operations similar to that described herein with regard to the QMA cartridge (e.g., TRAP and ELUTE operations).

Quality Control (QC)

The radiochemical purity and identity of the obtained product was confirmed by performing reverse-phase HPLC. The retention time for the radioactive peak produced by the product was compared to the FDHT reference standard peak retention time to confirm the radiochemical identity. Additional testing included visual inspection, pH, radionuclidic identity via half-life determination, filter integrity testing, determination of residual solvents by gas chromatography, and endotoxin level determination and sterility. The obtained results conform to the FDHT acceptance specifications established at Memorial Sloan Kettering Cancer Center (MSKCC) Radiochemistry and Molecular Imaging Probes Core for routine manual production of $^{18}$F-FDHT.

Figure 9A:
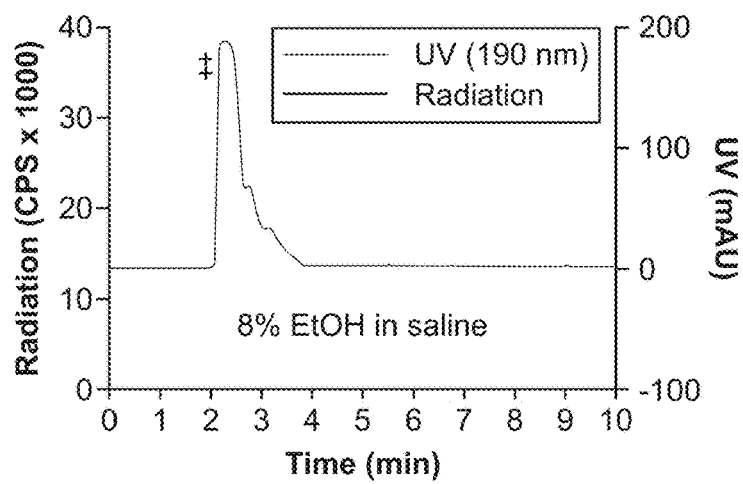
FIG. 9A illustrates a chromatogram of 8% EtOH/saline solution used for reformulation to determine peaks resulting from solvent effects.
Figure 9B:
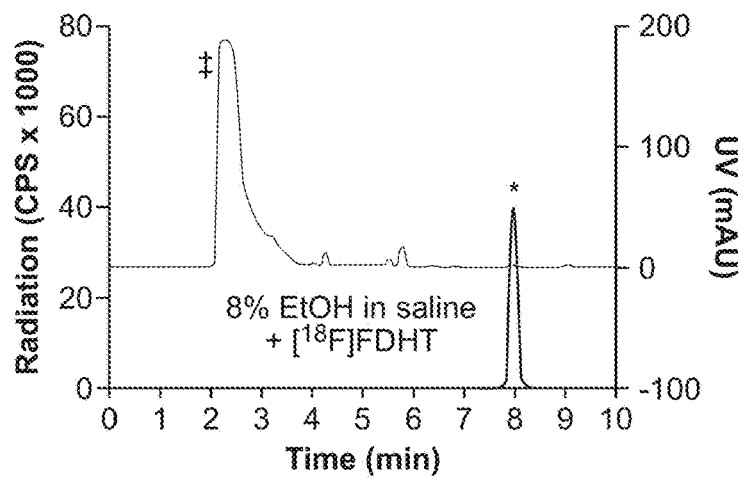
FIG. 9B illustrates a chromatogram of 8% EtOH/saline solution with the reformulated $^{18}$F-FDHT (and without the cold standard).
Figure 9C:
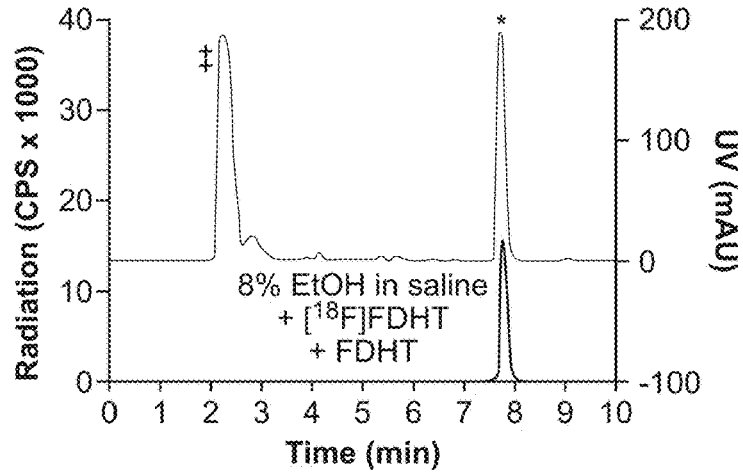
FIG. 9C illustrates a chromatogram of 8% EtOH/saline solution with the reformulated $^{18}$F-FDHT (and with the cold standard).

Results Decay-corrected radiochemical yield (RCY) was 29±5% (n=7) and was determined by dividing the reformulated activity by the initial starting activity. After automation of the synthesis, validation runs (n=6) yielded 9-33 mCi (0.33-1.2 GBq) starting from 77-179 mCi (2.8-6.6 GBq). To establish suitability for larger scale production, another synthesis was performed (n=1) starting with 1.0 Ci (37 GBq) of activity that resulted in 189 mCi (7.0 GBq) of $^{18}$F-FDHT after reformulation (32% decay-corrected yield), sufficient for multiple human patient doses. Overall synthesis time was 90 min: synthesis (56 min), purification (20 min), and reformulation of the product for injection (14 min). Specific activity was 1.5±0.1 Ci/µmol (55±4 GBq/µmol) (n=3) at the end of formulation using starting activities of synthesis from 77-92 mCi (2.8-3.4 GBq). The high activity synthesis resulted in a specific activity of 4.6 Ci/µmol (170 GBq/µmol) at the end of formulation. Approximately 5% of the decay-corrected starting activity was lost during reformulation to the sterile filter (4%) and the transfer line (1%), which was determined, after removal of the sterile filter and formulated product vial, by rinsing the pear flask and subsequent fluid lines with acetonitrile. Additional decay-corrected losses during synthesis (e.g., residue in vials, cartridges, transfer lines) were minimal, accounting for <10% of the starting activity. Analytical HPLC was first performed on the EtOH/saline solution used for reformulation to determine peaks resulting from solvent effects. Sample chromatograms of this along with the reformulated $^{18}$F-FDHT, with and without cold standard, are shown in FIGS. 9A-9C. All clinical-level QC test results were in full accordance with cGMP specifications in place at MSKCC (Table 6).

TABLE 6

| Clinical QC test | MSKCC acceptance criteria | Results |
| --- | --- | --- |
| Optical clarity | Clear and particle free | Clear and particle free |
| pH | 5.5-8.0 | 5.5-6.0 |
| Radiochemical purity | >95% | 98% |
| Radiochemical identity | Matches retention time of the standard | Matches retention time of the standard |
| F18 radionuclide identity | Half-life 105-115 min | 111 min |
| Endotoxin level (LAL) | <5 EU/mL | 0.318 EU/mL |
| Filter integrity | >50 psig | 51 psig |
| Ethanol content | <10% (100,000 ppm) | 70,000-80,000 ppm |
| Sterility | No growth in 14 days | No growth in 14 days |

Discussion

The fluorinated AR-binding ligand $^{18}$F-FDHT has great potential for both research and clinical investigations in the management of metastatic prostate cancer. The automated synthesis of $^{18}$F-FDHT described herein will allow for routine production of this PET tracer at multiple facilities. With the development of a reagent kit for $^{18}$F-FDHT and the use of disposable cassettes, a technician can perform the synthesis quickly and reproducibly. This is a significant advantage over the current, manual production of $^{18}$F-FDHT, which requires manual preparation of reagents and a highly experienced production radiochemist to perform the synthesis.

Due to the highly reactive nature of LiAlH$_4$, the reduction step is highly exothermic and, in the manual synthesis, is performed at −78° C. to tame the reactivity of the reducing reagent and to also minimize the formation of undesirable side products. Since cryogenic cooling is not available on commercial radiosynthesizers for $^{18}$F-labeled PET tracers, this step has previously hindered automation of the $^{18}$F-FDHT synthesis. To avoid the need for cryogenic conditions while utilizing LiAlH$_4$, the reducing agent is slowly added to minimize the rate of heat generation and potential side product formation.

In the reduction of ketone (intermediate 2) with LiAlH$_4$, a potential side product that could occur at increased temperature is the reduction of the C—F bond. Alkyl halides can be reduced by LiAlH$_4$ in ethereal solvents; however, the rates of reduction markedly decrease from iodide to bromide to chloride (I>Br>Cl) and from primary>secondary>tertiary halides, thus defluorination was not expected to be significant. In fact, a kinetic study of LiAlH$_4$ reductions at room temperature in THF with various alky halides illustrated that cyclopentyl bromide, which is a more reactive model for the cyclopentyl fluoride (intermediate 2), underwent only 11% reduction after 30 min at room temperature and required 24 h to fully reduce. The trend in alkyl halide reactivity rates, in addition to the short reaction time of intermediate 2 with LiAlH$_4$ (i.e., 20 s), suggests that the C—F bond would be stable under such reaction conditions. As expected, radio-TLC samples taken before and after the LiAlH$_4$ reduction to assess the respective ratios between highly polar radioactive compounds (e.g., free $^{18}$F-fluoride) and $^{18}$F-fluorinated compounds remained unchanged.

A time course for the LiAlH$_4$ reaction was performed and reduction of ketone (intermediate 2) was observed (via analytical HPLC) to be complete after 20 s of stirring, and thus the reaction was quenched with an acetone-THF solution 20 s after the LiAlH$_4$ addition. Quenching sooner resulted in an additional minor radioactive peak in the HPLC trace that matched the retention time of ketone (intermediate 2), indicating an incomplete reduction. The amount of acetone was optimized to fully quench excess LiAlH$_4$ without causing a large exotherm in the reaction vial. Too much acetone resulted in a rapid exotherm and the formation of significant aluminum salt deposits on the surface of the vial, which, was hypothesized, was the reason for substantial retention of up to 11% of the decay-corrected starting activity on the reaction vial. In addition, retention of the desired intermediate 3 on the inside walls of the vial led to inefficient deprotection in the subsequent step due to the inability of the HCl solution to reach the top of the vial; intermediate 3 was observed via analytical HPLC after aqueous extraction and during the purification of the final product. On the contrary, insufficient acetone left excess LiAlH$_4$ in the reaction mixture resulting in a similar exotherm during the acid-deprotection step. Significantly reduced salt deposition and increased reproducibility of yields were obtained when using 0.10 mL of acetone diluted with 0.25 mL of THF. This ratio was chosen to maintain a sufficient reagent volume for reliable addition to the reaction vessel and also to maintain the 0.35 mL volume utilized in the original manual synthesis. Under these conditions, the exotherm was controlled. Visual inspection of the diluted acetone quench revealed minimal splashing of material on the vial, the loss of activity stuck on the reaction vial was notably decreased to <2%, and the presence of ketal 3 during HPLC purification was substantially lowered.

Additional minor improvements were made to better automate other aspects of the manual synthesis to the ELIXYS radiosynthesizer. For example, the use of 9 mL vs. 15 mL of water was sufficient to transfer product to the HLB cartridge for the aqueous extraction and subsequently rinse the cartridge. Lowering the required water volume decreased the overall synthesis time by minimizing the operations needed to add and transfer the water. Also, the configuration of drying cartridges was modified in order to prevent potential blockage of the fluid pathway from Cassette 1 to Cassette 2. Initial attempts to solely use MgSO$_4$ as done at MSKCC were unsuccessful due to rapid hardening of the drying agent, consequently obstructing the flow. After testing both type and quantity of drying agents, we found that initially using the milder drying agent, Na$_2$SO$_4$, removed the majority of water from the organic solution, allowing more rigorous drying via MgSO$_4$ to occur reliably without hindering the flow. Of course, as explained herein, both drying agents Na$_2$SO$_4$ and MgSO$_4$ may be omitted entirely if a normal-phase HPLC is used.

Taken together, these measures avoid the need for cryogenic conditions and enabled complete automation of the synthesis, while still resulting in a useful RCY. The RCY we obtained was only modestly lower than the RCY of the manual procedure currently performed at MSKCC (16% vs. 22%). Moreover, specific activities greater than 1 Ci/µmol (37 GBq/µmol) were obtained and multiple clinical doses could be produced. This point was validated with a production run performed using 1.0 Ci of starting activity that yielded $^{18}$F-FDHT (189 mCi, 7.0 GBq) with increased specific activity (4.6 Ci/µmol, 169 GBq/µmol), sufficient for multiple patient doses. Combined with the formulated product having passed all clinical-level QC requirements, the synthesis is suitable for direct use in clinical production. Much larger starting activities are routinely available from cyclotrons if larger quantities of $^{18}$F-FDHT are desired.

With the ELIXYS radiosynthesizer, we have successfully automated $^{18}$F-FDHT synthesis. Recent reports have shown the potential for modification of the conventional synthesis methodology to eliminate the use of LiAlH$_4$ and normal-phase HPLC purification. The primary goal of these changes is to eventually enable a facile translation of the $^{18}$F-FDHT synthesis onto commercial automated synthesizers (e.g., GE TRACERlab™). Alterations to the synthesis protocol have been presented as conference abstracts in which, for example, reverse-phase HPLC purification was implemented to allow for rapid and straightforward reformulation using C18 solid-phase extraction after purification. See Nickels et al., Advances towards the optimization of 18F-fluorodihydrotestosterone for use in pre-clinical prostate imaging, World Molecular Imaging Meeting Abstracts (2014). In addition, the use of NaBH$_4$ as a milder reducing agent was recently optimized in the manual synthesis of $^{18}$F-FDHT to avoid cryogenic conditions. Zhou et al., Optimization of the preparation of fluorine-18-labeled steroid receptor ligands 16alpha-[18F]fluoroestradiol (FES), [18F] fluoro furanyl norprogesterone (FFNP), and 16beta-[18F] fluoro-5alpha-dihydrotestosterone (FDHT) as radiopharmaceuticals, J. Label Compd. Radiopharm 57, 371-377 (2014). Under this protocol the reduction step was performed at room temperature in ethanol and was complete after 10 min. However, prolonged stirring of the reaction mixture in the presence of acetone was required to quench excess NaBH$_4$; this critical step avoids significant decomposition of the desired product during the subsequent acid mediated deprotection. While the slow decomposition of NaBH$_4$ in protic solvents to form H$_2$ gas is an insignificant concern at the time-scale of the reduction, this incompatibility creates a limitation with regard to reagent preparation and automation of this protocol. The requirement to prepare a fresh NaBH$_4$ solution before each synthesis limits the practicality of commercially available reagent kits to be provided for the automated synthesis of $^{18}$F-FDHT. Furthermore, the low solubility of NaBH$_4$ in alcoholic solvents may result in complications of reagent addition (e.g., clogging) during use in commercial automated synthesizers.

Ultimately, NaBH$_4$ and reverse-phase HPLC were not used herein to: 1) accelerate translation to an automated protocol by avoiding significant re-optimization of these steps, and 2) demonstrate that LiAlH$_4$ reduction and normal-phase HPLC purification are possible using the ELIXYS radiosynthesizer, further demonstrating the system's versatility. Of course, simplifications or improvements to the $^{18}$F-FDHT synthesis protocol could quickly be applied to the ELIXYS radiosynthesizer if desired. The radiosynthesis of $^{18}$F-FDHT has been adapted for full automation on the ELIXYS radiosynthesizer resulting in good yields, high purity and good specific activity suitable for clinical use. In addition to the advantages of automation, the use of disposable kits on ELIXYS facilitates the creation of reagent kits that will enable widespread access to this promising PET tracer and potentially aid in the clinical management of metastatic prostate cancer.

While embodiments of the present invention have been shown and described, various modifications may be made without departing from the scope of the present invention. The invention, therefore, should not be limited except to the following claims and their equivalents.

What is claimed is:
1. A method for the automated synthesis of 16β-$^{18}$F-fluoro-5α-dihydrotestosterone ($^{18}$F-FDHT) comprising:
   loading a plurality of reagents in an automated radiosynthesizer, the automated radiosynthesizer comprising a cassette and a reactor disposed beneath the cassette, wherein at least some of the reagents are stored on the cassette;
   executing a synthesis program on the automated radiosynthesizer, the synthesis program comprising:
      eluting $^{18}$F-fluoride into a reactor vial contained in the reactor via the cassette;
      adding acetonitrile reagent via the cassette into the reactor vial and evaporating the contents thereof with the reactor;
      cooling the reactor vial and adding a precursor solution comprising 16α-[[(trifluoromethyl)sulfonyl]oxy]-3,3-(ethylenedioxy)androstan-17-one via the cassette;
      reacting the precursor solution within the reactor vial at elevated temperature under stirring conditions;
      cooling the reactor vial to approximately room temperature and adding a solution of LiAlH$_4$ via the cassette followed by stirring;
      adding acetone-THF solution into the reactor vial via the cassette followed by stirring;
      adding HCl solution into the reactor vial via the cassette and reacting the same at elevated temperature under stirring conditions;
      cooling the reactor vial and transferring the contents through a hydrophilic-lipophilic balanced (HLB) cartridge so as to trap product therein;
      rinsing the reaction container and the HLB cartridge with water;
      drying the HLB cartridge under an inert gas; and
      passing dichloromethane (DCM) reagent into the HLB cartridge so as to elute $^{18}$F-FDHT from the HLB cartridge.

2. The method of claim 1, further comprising transferring the $^{18}$F-FDHT into a HPLC loop associated with the automated radiosynthesizer to purify the $^{18}$F-FDHT.

3. The method of claim 2, further comprising reformulating the purified $^{18}$F-FDHT with ethanol and sterile saline.

4. A method for the automated synthesis of 16β-$^{18}$F-fluoro-5α-dihydrotestosterone ($^{18}$F-FDHT) comprising:
   loading a plurality of reagents in an automated radiosynthesizer, the radiosynthesizer comprising a first reactor, a second reactor, a first cassette disposed above the first reactor, and a second cassette disposed above the second reactor, wherein each of the first and second cassettes define fluid passageways for reagents and reaction products and provide respective contact surfaces for vials respectively contained in the first and second reactors;

executing a synthesis program on the automated radiosynthesizer, the synthesis program comprising:
  eluting $^{18}$F-fluoride into the vial of the first reactor through the first cassette;
  adding acetonitrile into the vial of the first reactor through the first cassette;
  contacting the vial of the first reactor against the first cassette and evaporating the contents;
  cooling the vial of the first reactor and adding a precursor solution comprising 16α-[[(trifluoromethyl)sulfonyl]oxy]-3,3-(ethylenedioxy)androstan-17-one through the first cassette;
  heating the precursor solution within the vial of the first reactor at elevated temperature under stirring conditions;
  cooling the vial of the first reactor to approximately room temperature and adding a solution of LiAlH$_4$ via the first cassette followed by stirring;
  adding acetone-THF solution via the first cassette into the vial of the first reactor followed by stirring;
  adding HCl solution via the first cassette and heating to elevated temperature under stirring conditions;
  cooling the vial of the first reactor and transferring the contents through a hydrophilic-lipophilic balanced (HLB) cartridge coupled to the first cassette so as to trap product therein and transferring waste $^{18}$F-fluoride to a waste vial coupled to the first cassette;
  rinsing the vial of the first reactor and the HLB cartridge with water via the first cassette;
  drying the HLB cartridge under an inert gas;
  passing dichloromethane (DCM) through the first cassette and into the HLB cartridge so as to elute $^{18}$F-FDHT from the HLB cartridge and transferring the same to the vial of the second reactor via the second cassette; and
  transferring the contents of the vial of the second reactor via the second cassette into an HPLC loop associated with the automated radiosynthesizer to purify the $^{18}$F-FDHT.

5. The method of claim 4, further comprising reformulating the purified $^{18}$F-FDHT with ethanol and sterile saline.

6. The method of claim 4, wherein the acetonitrile, precursor solution, LiAlH$_4$ solution, HCl solution, rinse water solution are stored in vials disposed on the first cassette.

7. The method of claim 4, wherein the synthesis program comprises a sequence of synthesis operations stored as instructions within computer software associated with the automated radiosynthesizer and the automated radiosynthesizer executes the synthesis operations automatically without operator involvement in accordance with the stored instructions.

8. The method of claim 4, wherein the addition of LiAlH$_4$ solution and acetone-THF solution are added at a rate lower than the rate of addition of other reagents.

9. The method of claim 4, wherein the acetone-THF solution comprises about 0.10 mL of acetone diluted with 0.25 mL of THF or an equivalent volumetric fraction.

10. The method of claim 4, wherein the acetone-THF solution is added after about 20 seconds after the addition of the LiAlH$_4$ solution.

11. The method of claim 4, wherein the output of the HLB cartridge is coupled to at least one downstream desiccant cartridge comprising a Na$_2$SO$_4$ cartridge.

12. The method of claim 11, wherein the at least one downstream desiccant cartridge further comprises a MgSO$_4$ cartridge.

13. The method of claim 4, wherein the $^{18}$F-FDHT has specific activity greater than 1 Ci/μmol.

14. The method of claim 4, wherein the vial of the first reactor that contains the added HCL solution is contacted with a contact surface of the first cartridge.

* * * * *